(12) United States Patent
Iwai

(10) Patent No.: US 8,546,094 B2
(45) Date of Patent: Oct. 1, 2013

(54) UBIQUITIN LIGASE AND USE THEREOF

(75) Inventor: Kazuhiro Iwai, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 13/389,065

(22) PCT Filed: Aug. 6, 2010

(86) PCT No.: PCT/JP2010/063345
§ 371 (c)(1),
(2), (4) Date: Feb. 27, 2012

(87) PCT Pub. No.: WO2011/016540
PCT Pub. Date: Feb. 10, 2011

(65) Prior Publication Data
US 2012/0145544 A1 Jun. 14, 2012

(30) Foreign Application Priority Data
Aug. 7, 2009 (JP) ................................. 2009-184878

(51) Int. Cl.
*C12Q 1/25* (2006.01)
*C12N 9/00* (2006.01)

(52) U.S. Cl.
USPC .......................................... 435/7.6; 435/183

(58) Field of Classification Search
None
See application file for complete search history.

(56) References Cited

PUBLICATIONS

Tokunaga et al., "SHARPIN is a component of the NF-kB-activating linear ubiquitin chain assembly complex", Nature 471:633-637, 2011.*
GenPept Accession No. Q96EP0, May 2013, 11 pages.*
GenPept Accession No. Q9BYM8, May 2013, 16 pages.*
GenPept Accession No. Q9H0F6, May 2013, 9 pages.*
English translation of International Preliminary Report on Patentability issued in corresponding PCT application No. PCT/JP2010/063345, 2011.
F. Tokunaga et al., "Involvement of Linear Polyubiquitylatoin of NEMO in NF-kB Activation", Nature Cell Biology, vol. 11, No. 2, pp. 123-132, Feb. 2009.
T. Kirisako et al., "A Ubiquitin Ligase Complex Assembles Linear Polyubiquitin Chains", The EMBO Journal, vol. 25, No. 20, pp. 4877-4887, 2006.
R. W. Seymour et al., "Spontaneous Mutations in the Mouse Sharpin Gene Result in Multiorgan Inflammation, Immune System Dysregulation and Dermatitis", Genes and Immunity, vol. 8, pp. 416-421, 2007.
F. Tokunaga et al., "Involvement of LUBAC-Mediated Linear Polyubiquitination of Nemo in NF-kB Activation", Protein, Nucleic Acid and Enzyme, vol. 54, No. 5, pp. 1-27, 2009 (with English translation).
K. Iwai et al., "Linear Polyubiquitination: A New Regulator of NF-kB Activation", EMBO Reports, vol. 10, No. 7, pp. 706-713, 2009.
Database DDBJ/EMBL/GenBank [online], Accession No. NM_030974, A Vega et al., Definition: *Homo sapiens* SHANK-Associated RH Domain Interactor (SHARPIN), mRNA, 2008.
Extended European Search Report issued Jun. 18, 2013 in corresponding European Patent Application No. 10806539.2.
Fumiyo Ikeda et al., "SHARPIN forms a linear ubiquitin ligase complex regulating NF-κB activity and apoptosis", vol. 471, No. 7340, Mar. 31, 2011, pp. 637-641, XP55066002.
Carolina Grabbe et al., "Functional Roles of Ubiquitin-Like Domain (ULD) and Ubiquitin-Binding Domain (UBD) Containing Proteins", Chemical Reviews, vol. 109, No. 4, Apr. 8, 2009, pp. 1481-1494, XP55066183.

\* cited by examiner

*Primary Examiner* — David J Steadman
(74) *Attorney, Agent, or Firm* — Wenderoth, Lind & Ponack, L.L.P.

(57) ABSTRACT

Provided is a novel ubiquitin ligase which has linear polyubiquitination activity and can be efficiently expressed and purified. It was found out that a complex of
(a) a protein having a part of HOIP and at least having a UBA region and a RING-IBR-RING region thereof, and
(b) One or more kinds of proteins which individually form a complex with the above (a)
is a novel ubiquitin ligase which has linear polyubiquitination activity and can be efficiently expressed and purified.

2 Claims, 5 Drawing Sheets

Petit-LUBAC

CBB staining

Petit-Sharpin

SEQUENCE LISTING

```
<160> NUMBER OF SEQ ID NOS: 13

<210> SEQ ID NO 1
<211> LENGTH: 510
<212> TYPE: PRT
<213> ORGANISM: Homo sapiens

<400> SEQUENCE: 1

Met Asp Glu Lys Thr Lys Lys Ala Glu Glu Met Ala Leu Ser Leu Thr
1               5                   10                  15

Arg Ala Val Ala Gly Gly Asp Glu Gln Val Ala Met Lys Cys Ala Ile
            20                  25                  30

Trp Leu Ala Glu Gln Arg Val Pro Leu Ser Val Gln Leu Lys Pro Glu
        35                  40                  45

Val Ser Pro Thr Gln Asp Ile Arg Leu Trp Val Ser Val Glu Asp Ala
    50                  55                  60

Gln Met His Thr Val Thr Ile Trp Leu Thr Val Arg Pro Asp Met Thr
65                  70                  75                  80

Val Ala Ser Leu Lys Asp Met Val Phe Leu Asp Tyr Gly Phe Pro Pro
                85                  90                  95

Val Leu Gln Gln Trp Val Ile Gly Gln Arg Leu Ala Arg Asp Gln Glu
            100                 105                 110

Thr Leu His Ser His Gly Val Arg Gln Asn Gly Asp Ser Ala Tyr Leu
        115                 120                 125

Tyr Leu Leu Ser Ala Arg Asn Thr Ser Leu Asn Pro Gln Glu Leu Gln
    130                 135                 140
```

```
Arg Glu Arg Gln Leu Arg Met Leu Glu Asp Leu Gly Phe Lys Asp Leu
145                 150                 155                 160

Thr Leu Gln Pro Arg Gly Pro Leu Glu Pro Gly Pro Pro Lys Pro Gly
                165                 170                 175

Val Pro Gln Glu Pro Gly Arg Gly Gln Pro Asp Ala Val Pro Glu Pro
            180                 185                 190

Pro Pro Val Gly Trp Gln Cys Pro Gly Cys Thr Phe Ile Asn Lys Pro
        195                 200                 205

Thr Arg Pro Gly Cys Glu Met Cys Cys Arg Ala Arg Pro Glu Ala Tyr
    210                 215                 220

Gln Val Pro Ala Ser Tyr Gln Pro Asp Glu Glu Arg Ala Arg Leu
225                 230                 235                 240

Ala Gly Glu Glu Glu Ala Leu Arg Gln Tyr Gln Arg Lys Gln Gln
                245                 250                 255

Gln Gln Glu Gly Asn Tyr Leu Gln His Val Gln Leu Asp Gln Arg Ser
            260                 265                 270

Leu Val Leu Asn Thr Glu Pro Ala Glu Cys Pro Val Cys Tyr Ser Val
        275                 280                 285

Leu Ala Pro Gly Glu Ala Val Val Leu Arg Glu Cys Leu His Thr Phe
    290                 295                 300

Cys Arg Glu Cys Leu Gln Gly Thr Ile Arg Asn Ser Gln Glu Ala Glu
305                 310                 315                 320

Val Ser Cys Pro Phe Ile Asp Asn Thr Tyr Ser Cys Ser Gly Lys Leu
                325                 330                 335

Leu Glu Arg Glu Ile Lys Ala Leu Leu Thr Pro Glu Asp Tyr Gln Arg
            340                 345                 350

Phe Leu Asp Leu Gly Ile Ser Ile Ala Glu Asn Arg Ser Ala Phe Ser
        355                 360                 365

Tyr His Cys Lys Thr Pro Asp Cys Lys Gly Trp Cys Phe Phe Glu Asp
    370                 375                 380

Asp Val Asn Glu Phe Thr Cys Pro Val Cys Phe His Val Asn Cys Leu
385                 390                 395                 400

Leu Cys Lys Ala Ile His Glu Gln Met Asn Cys Lys Glu Tyr Gln Glu
                405                 410                 415

Asp Leu Ala Leu Arg Ala Gln Asn Asp Val Ala Ala Arg Gln Thr Thr
            420                 425                 430

Glu Met Leu Lys Val Met Leu Gln Gln Gly Glu Ala Met Arg Cys Pro
        435                 440                 445

Gln Cys Gln Ile Val Val Gln Lys Lys Asp Gly Cys Asp Trp Ile Arg
    450                 455                 460

Cys Thr Val Cys His Thr Glu Ile Cys Trp Val Thr Lys Gly Pro Arg
465                 470                 475                 480

Trp Gly Pro Gly Gly Pro Gly Asp Thr Ser Gly Gly Cys Arg Cys Arg
                485                 490                 495

Val Asn Gly Ile Pro Cys His Pro Ser Cys Gln Asn Cys His
            500                 505                 510

<210> SEQ ID NO 2
<211> LENGTH: 1533
<212> TYPE: DNA
<213> ORGANISM: Homo sapiens

<400> SEQUENCE: 2
atggacgaga agaccaagaa agcagaggaa atggccctga gcctcacccg agcagtggcg    60
```

-continued

```
ggcggggatg aacaggtggc aatgaagtgt gccatctggc tggcagagca acgggtgccc    120
ctgagtgtgc aactgaagcc tgaggtctcc ccaacgcagg acatcaggct gtgggtgagc    180
gtggaggatg ctcagatgca caccgtcacc atctggctca cagtgcgccc tgatatgaca    240
gtggcgtctc tcaaggacat ggttttctg gactatggct ccccaccagt cttgcagcag     300
tgggtgattg gcagcggct ggcacgagac caggagaccc tgcactccca tggggtgcgg     360
cagaatgggg acagtgccta cctctatctg ctgtcagccc gcaacacctc cctcaaccct    420
caggagctgc agcgggagcg gcagctgcgg atgctggaag atctgggctt caaggacctc    480
acgctgcagc cgcggggccc tctggagcca ggccccccaa agcccggggt ccccaggaa     540
cccggacggg ggcagccaga tgcagtgcct gagcccccac cggtgggctg cagtgccccc    600
gggtgcacct tcatcaacaa gcccacgcgg cctggctgtg agatgtgctg ccgggcgcgc    660
cccgaggcct accaggtccc cgcctcatac cagcccgacg aggaggagcg agcgcgcctg    720
gcgggcgagg aggaggcgct gcgtcagtac cagcagcgga agcagcagca caggagggg    780
aactacctgc agcacgtcca gctggaccag aggagcctgg tgctgaacac ggagcccgcc    840
gagtgccccg tgtgctactc ggtgctggcg cccggcgagg ccgtggtgct gcgtgagtgt    900
ctgcacacct tctgcaggga gtgcctgcag ggcaccatcc gcaacagcca ggaggcggag    960
gtctcctgcc ccttcattga caacacctac tcgtgctcgg gcaagctgct ggagagggag    1020
atcaaggcgc tcctgacccc tgaggattac cagcgatttc tagacctggg catctccatt    1080
gctgaaaacc gcagtgcctt cagctaccat tgcaagaccc agattgcaa gggatggtgc     1140
ttctttgagg atgatgtcaa tgagttcacc tgccctgtgt gtttccacgt caactgcctg    1200
ctctgcaagg ccatccatga gcagatgaac tgcaaggagt atcaggagga cctggccctg    1260
cgggctcaga cgatgtggc tgcccggcag acgacagaga tgctgaaggt gatgctgcag    1320
cagggcgagg ccatgcgctg cccccagtgc cagatcgtgg tacagaagaa ggacggctgc    1380
gactggatcc gctgcaccgt ctgccacacc gagatctgct gggtcaccaa gggcccacgc    1440
tggggccctg ggggcccagg agacaccagc ggggctgcc gctgcagggt aaatgggatt    1500
ccttgccacc caagctgtca gaactgccac tga    1533
```

<210> SEQ ID NO 3
<211> LENGTH: 1072
<212> TYPE: PRT
<213> ORGANISM: Homo sapiens

<400> SEQUENCE: 3

```
Met Pro Gly Glu Glu Glu Arg Ala Phe Leu Val Ala Arg Glu Glu
1               5                   10                  15

Leu Ala Ser Ala Leu Arg Arg Asp Ser Gly Gln Ala Phe Ser Leu Glu
                20                  25                  30

Gln Leu Arg Pro Leu Leu Ala Ser Ser Leu Pro Leu Ala Ala Arg Tyr
            35                  40                  45

Leu Gln Leu Asp Ala Ala Arg Leu Val Arg Cys Asn Ala His Gly Glu
        50                  55                  60

Pro Arg Asn Tyr Leu Asn Thr Leu Ser Thr Ala Leu Asn Ile Leu Glu
65                  70                  75                  80

Lys Tyr Gly Arg Asn Leu Leu Ser Pro Gln Arg Pro Tyr Trp Arg
                85                  90                  95

Gly Val Lys Phe Asn Asn Pro Val Phe Arg Ser Thr Val Asp Ala Val
                100                 105                 110

Gln Gly Gly Arg Asp Val Leu Arg Leu Tyr Gly Tyr Thr Glu Glu Gln
```

-continued

```
            115                 120                 125
Pro Asp Gly Leu Ser Phe Pro Glu Gly Gln Glu Pro Asp Glu His
            130                 135                 140
Gln Val Ala Thr Val Thr Leu Glu Val Leu Leu Arg Thr Glu Leu
145                 150                 155                 160
Ser Leu Leu Leu Gln Asn Thr His Pro Arg Gln Ala Leu Glu Gln
                    165                 170                 175
Leu Leu Glu Asp Lys Val Glu Asp Met Leu Gln Leu Ser Glu Phe
                180                 185                 190
Asp Pro Leu Leu Arg Glu Ile Ala Pro Gly Pro Leu Thr Thr Pro Ser
                    195                 200                 205
Val Pro Gly Ser Thr Pro Gly Pro Cys Phe Leu Cys Gly Ser Ala Pro
210                 215                 220
Gly Thr Leu His Cys Pro Ser Cys Lys Gln Ala Leu Cys Pro Ala Cys
225                 230                 235                 240
Asp His Leu Phe His Gly His Pro Ser Arg Ala His His Leu Arg Gln
                    245                 250                 255
Thr Leu Pro Gly Val Leu Gln Gly Thr His Leu Ser Pro Ser Leu Pro
                260                 265                 270
Ala Ser Ala Gln Pro Arg Pro Gln Ser Thr Ser Leu Leu Ala Leu Gly
            275                 280                 285
Asp Ser Ser Leu Ser Ser Pro Asn Pro Ala Ser Ala His Leu Pro Trp
            290                 295                 300
His Cys Ala Ala Cys Ala Met Leu Asn Glu Pro Trp Ala Val Leu Cys
305                 310                 315                 320
Val Ala Cys Asp Arg Pro Arg Gly Cys Lys Gly Leu Gly Leu Gly Thr
                    325                 330                 335
Glu Gly Pro Gln Gly Thr Gly Gly Leu Glu Pro Asp Leu Ala Arg Gly
                340                 345                 350
Arg Trp Ala Cys Gln Ser Cys Thr Phe Glu Asn Glu Ala Ala Ala Val
                355                 360                 365
Leu Cys Ser Ile Cys Glu Arg Pro Arg Leu Ala Gln Pro Pro Ser Leu
    370                 375                 380
Val Val Asp Ser Arg Asp Ala Gly Ile Cys Leu Gln Pro Leu Gln Gln
385                 390                 395                 400
Gly Asp Ala Leu Leu Ala Ser Ala Gln Ser Gln Val Trp Tyr Cys Ile
                    405                 410                 415
His Cys Thr Phe Cys Asn Ser Ser Pro Gly Trp Val Cys Val Met Cys
                420                 425                 430
Asn Arg Thr Ser Ser Pro Ile Pro Ala Gln His Ala Pro Arg Pro Tyr
            435                 440                 445
Ala Ser Ser Leu Glu Lys Gly Pro Pro Lys Pro Gly Pro Pro Arg Arg
450                 455                 460
Leu Ser Ala Pro Leu Pro Ser Ser Cys Gly Asp Pro Glu Lys Gln Arg
465                 470                 475                 480
Gln Asp Lys Met Arg Glu Glu Gly Leu Gln Leu Val Ser Met Ile Arg
                485                 490                 495
Glu Gly Glu Ala Ala Gly Ala Cys Pro Glu Glu Ile Phe Ser Ala Leu
                500                 505                 510
Gln Tyr Ser Gly Thr Glu Val Pro Leu Gln Trp Leu Arg Ser Glu Leu
            515                 520                 525
Pro Tyr Val Leu Glu Met Val Ala Glu Leu Ala Gly Gln Gln Asp Pro
530                 535                 540
```

-continued

```
Gly Leu Gly Ala Phe Ser Cys Gln Glu Ala Arg Arg Ala Trp Leu Asp
545                 550                 555                 560

Arg His Gly Asn Leu Asp Glu Ala Val Glu Cys Val Arg Thr Arg
            565                 570                 575

Arg Arg Lys Val Gln Glu Leu Gln Ser Leu Gly Phe Gly Pro Glu Glu
            580                 585                 590

Gly Ser Leu Gln Ala Leu Phe Gln His Gly Gly Asp Val Ser Arg Ala
            595                 600                 605

Leu Thr Glu Leu Gln Arg Gln Arg Leu Glu Pro Phe Arg Gln Arg Leu
610                 615                 620

Trp Asp Ser Gly Pro Glu Pro Thr Pro Ser Trp Asp Gly Pro Asp Lys
625                 630                 635                 640

Gln Ser Leu Val Arg Arg Leu Leu Ala Val Tyr Ala Leu Pro Ser Trp
                645                 650                 655

Gly Arg Ala Glu Leu Ala Leu Ser Leu Leu Gln Glu Thr Pro Arg Asn
                660                 665                 670

Tyr Glu Leu Gly Asp Val Val Glu Ala Val Arg His Ser Gln Asp Arg
                675                 680                 685

Ala Phe Leu Arg Arg Leu Leu Ala Gln Glu Cys Ala Val Cys Gly Trp
690                 695                 700

Ala Leu Pro His Asn Arg Met Gln Ala Leu Thr Ser Cys Glu Cys Thr
705                 710                 715                 720

Ile Cys Pro Asp Cys Phe Arg Gln His Phe Thr Ile Ala Leu Lys Glu
                725                 730                 735

Lys His Ile Thr Asp Met Val Cys Pro Ala Cys Gly Arg Pro Asp Leu
                740                 745                 750

Thr Asp Asp Thr Gln Leu Leu Ser Tyr Phe Ser Thr Leu Asp Ile Gln
                755                 760                 765

Leu Arg Glu Ser Leu Glu Pro Asp Ala Tyr Ala Leu Phe His Lys Lys
                770                 775                 780

Leu Thr Glu Gly Val Leu Met Arg Asp Pro Lys Phe Leu Trp Cys Ala
785                 790                 795                 800

Gln Cys Ser Phe Gly Phe Ile Tyr Glu Arg Glu Gln Leu Glu Ala Thr
                805                 810                 815

Cys Pro Gln Cys His Gln Thr Phe Cys Val Arg Cys Lys Arg Gln Trp
                820                 825                 830

Glu Glu Gln His Arg Gly Arg Ser Cys Glu Asp Phe Gln Asn Trp Lys
                835                 840                 845

Arg Met Asn Asp Pro Glu Tyr Gln Ala Gln Gly Leu Ala Met Tyr Leu
850                 855                 860

Gln Glu Asn Gly Ile Asp Cys Pro Lys Cys Lys Phe Ser Tyr Ala Leu
865                 870                 875                 880

Ala Arg Gly Gly Cys Met His Phe His Cys Thr Gln Cys Arg His Gln
                885                 890                 895

Phe Cys Ser Gly Cys Tyr Asn Ala Phe Tyr Ala Lys Asn Lys Cys Pro
                900                 905                 910

Glu Pro Asn Cys Arg Val Lys Lys Ser Leu His Gly His His Pro Arg
                915                 920                 925

Asp Cys Leu Phe Tyr Leu Arg Asp Trp Thr Ala Leu Arg Leu Gln Lys
                930                 935                 940

Leu Leu Gln Asp Asn Asn Val Met Phe Asn Thr Glu Pro Pro Ala Gly
945                 950                 955                 960

Ala Arg Ala Val Pro Gly Gly Gly Cys Arg Val Ile Glu Gln Lys Glu
                965                 970                 975
```

```
Val Pro Asn Gly Leu Arg Asp Glu Ala Cys Gly Lys Glu Thr Pro Ala
            980                 985                 990

Gly Tyr Ala Gly Leu Cys Gln Ala  His Tyr Lys Glu Tyr  Leu Val Ser
        995                 1000                1005

Leu Ile  Asn Ala His Ser Leu  Asp Pro Ala Thr  Leu  Tyr Glu Val
    1010             1015                1020

Glu Glu  Leu Glu Thr Ala Thr  Glu Arg Tyr Leu His  Val Arg Pro
    1025             1030                1035

Gln Pro  Leu Ala Gly Glu Asp  Pro Pro Ala Tyr Gln  Ala Arg Leu
    1040             1045                1050

Leu Gln  Lys Leu Thr Glu Glu  Val Pro Leu Gly Gln  Ser Ile Pro
    1055             1060                1065

Arg Arg  Arg Lys
    1070

<210> SEQ ID NO 4
<211> LENGTH: 3219
<212> TYPE: DNA
<213> ORGANISM: Homo sapiens

<400> SEQUENCE: 4
atgccggggg aggaagagga gcgggccttc ctggtggccc gcgaggagct ggcgagcgcc    60
ctgaggaggg attccgggca ggcgttttcc ctggagcagc tccggccgct actagccagc   120
tctctgccgc tagccgcccg ctacctgcag ctggacgccg cacgccttgt ccgctgcaac   180
gctcatgggg agccccgaaa ctacctcaac accctgtcca cggctctgaa catcctggag   240
aaatacggcc gcaaccttct cagccctcag cggcctcggt actggcgtgg tgtcaagttt   300
aataaccctg tctttcgcag cacggtggat gctgtgcagg ggggccgaga tgtgctgcga   360
ttatatggct acacagagga gcaaccagat gggttgagct cccccgaagg gcaggaggag   420
ccagatgagc accaggttgc tacagtcaca ctggaagtac tgctgcttcg gacagagctc   480
agcctgctat tgcagaatac tcatccaaga cagcaggcac tggagcagct gttggaagac   540
aaggttgaag atgatatgct gcagctttca gaatttgacc ccctattgag agagattgct   600
cctggccccc tcaccacacc ctctgtccca ggctccactc ctggtccctg cttcctctgt   660
ggttctgccc caggcacact gcactgccca tcctgtaaac aggccctgtg tccagcctgt   720
gaccacctgt tccatggaca cccatcccgt gctcatcacc tccgccagac cctgcctggg   780
gtcctgcagg gtaccacct gagccccagt ttacctgcct cagcccaacc acggccccag   840
tcgacctccc tgctggccct gggagacagc tctctttctt cccctaatcc tgcaagtgct   900
catttgccct ggcactgtgc tgcctgtgcc atgctaaatg agccttgggc agtgctctgt   960
gtggcctgtg atcggccccg aggctgtaag gggttgggt tgggaactga gggtccccaa  1020
ggaactggag gcctagaacc tgatcttgca cgggtcggt gggcctgcca gagctgtacc  1080
tttgagaatg aggcagctgc tgtgctatgt tccatatgtg agcgacctcg gctggcccag  1140
cctcccagct tggtggtgga ttcccgagat gctggcattt gcctgcaacc ccttcagcag  1200
ggggatgctt tgctggcctc tgcccagagt caagtctggt actgtattca ctgtaccttc  1260
tgcaactcga gccctggctg ggtgtgtgtt atgtgcaacc ggactagtag ccccattcca  1320
gcacaacatg cccccggcc ctatgccagc tctttggaaa agggaccccc caagcctggg  1380
cccccacgac gccttagtgc ccccctgccc agttcctgtg agatcctga aagcagcgc  1440 caagacaaga tgcgggaaga aggcctccag ctagtgagca tgatccggga aggggaagcc  1500
```

-continued

```
gcaggtgcct gtccagagga gatcttctcg gctctgcagt actcgggcac tgaggtgcct    1560
ctgcagtggt tgcgctcaga actgccctac gtcctggaga tggtggctga gctggctgga    1620
cagcaggacc ctgggctggg tgccttttcc tgtcaggagg cccggagagc ctggctggat    1680
cgtcatggca accttgatga agctgtggag gagtgtgtga ggaccaggcg aaggaaggtg    1740
caggagctcc agtctctagg ctttgggcct gaggaggggt ctctccaggc attgttccag    1800 cacgaggtg atgtgtcacg ggccctgact gagctacagc gccaacgcct agagcccttc    1860
cgccagcgcc tctgggacag tggccctgag cccaccccttc cctgggatgg gccagacaag    1920
cagagcctgg tcaggcggct tttggcagtc tacgcactcc ccagctgggg ccgggcagag    1980
ctggcactgt cactgctgca ggagacaccc aggaactatg agttggggga tgtggtagaa    2040
gctgtgaggc acagccagga ccgggccttc ctgcgccgct tgcttgccca ggagtgtgcc    2100
gtgtgtggct gggccctgcc ccacaaccgg atgcaggccc tgacttcctg tgagtgcacc    2160
atctgtcctg actgcttccg ccagcacttc accatcgcct tgaaggagaa gcacatcaca    2220
gacatggtgt gccctgcctg tggccgcccc gacctcaccg atgacacaca gttgctcagc    2280
tacttctcta cccttgacat ccagcttcgc gagagcctag agccagatgc ctatgcgttg    2340
ttccataaga agctgaccga gggtgtgctg atgcgggacc ccaagttctt gtggtgtgcc    2400
cagtgctcct ttggcttcat atatgagcgt gagcagctgg aggcaacttg tccccagtgt    2460
caccagacct tctgtgtgcg ctgcaagcgc cagtgggagg agcagcaccg aggtcggagc    2520
tgtgaggact ccagaactg gaaacgcatg aacgacccag aataccaggc ccagggccta    2580
gcaatgtatc ttcaggaaaa cggcattgac tgccccaaat gcaagttctc gtacgccctg    2640
gcccgaggag gctgcatgca ctttcactgt acccagtgcc gccaccagtt ctgcagcggc    2700
tgctacaatg ccttttacgc caagaataaa tgtccagagc ctaactgcag ggtgaaaaag    2760
tccctgcacg gccaccaccc tcgagactgc ctcttctacc tgcgggactg gactgctctc    2820
cggcttcaga agctgctaca ggacaataac gtcatgtttta atacagagcc tccagctggg    2880
gcccgggcag tccctggagg cggctgccga gtgatagagc agaaggaggt tcccaatggg    2940
ctcagggacg aagcttgtgg caaggaaact ccagctggct atgccggcct gtgccaggca    3000
cactacaaag agtatcttgt gagcctcatc aatgcccact cgctggaccc agccaccttg    3060
tatgaggtgg aagagctgga cggccactg gagcgctacc tgcacgtacg cccccagcct    3120
ttggctggag aggatccccc tgcttaccag gcccgcttgt acagaagct gacagaagag    3180 gtacccttgg gacagagtat cccccgcagg cggaagtag                          3219
```

<210> SEQ ID NO 5
<211> LENGTH: 191
<212> TYPE: PRT
<213> ORGANISM: Homo sapiens

<400> SEQUENCE: 5

Met Asp Glu Lys Thr Lys Lys Ala Glu Glu Met Ala Leu Ser Leu Thr
1               5                   10                  15

Arg Ala Val Ala Gly Gly Asp Glu Gln Val Ala Met Lys Cys Ala Ile
                20                  25                  30

Trp Leu Ala Glu Gln Arg Val Pro Leu Ser Val Gln Leu Lys Pro Glu
            35                  40                  45

Val Ser Pro Thr Gln Asp Ile Arg Leu Trp Val Ser Val Glu Asp Ala
        50                  55                  60

Gln Met His Thr Val Thr Ile Trp Leu Thr Val Arg Pro Asp Met Thr
65                  70                  75                  80

Val Ala Ser Leu Lys Asp Met Val Phe Leu Asp Tyr Gly Phe Pro Pro
                85                  90                  95

Val Leu Gln Gln Trp Val Ile Gly Gln Arg Leu Ala Arg Asp Gln Glu
            100                 105                 110

Thr Leu His Ser His Gly Val Arg Gln Asn Gly Asp Ser Ala Tyr Leu
        115                 120                 125

Tyr Leu Leu Ser Ala Arg Asn Thr Ser Leu Asn Pro Gln Glu Leu Gln
    130                 135                 140

Arg Glu Arg Gln Leu Arg Met Leu Glu Asp Leu Gly Phe Lys Asp Leu
145                 150                 155                 160

Thr Leu Gln Pro Arg Gly Pro Leu Glu Pro Gly Pro Lys Pro Gly
                165                 170                 175

Val Pro Gln Glu Pro Gly Arg Gly Gln Pro Asp Ala Val Pro Glu
            180                 185                 190

<210> SEQ ID NO 6
<211> LENGTH: 576
<212> TYPE: DNA
<213> ORGANISM: Homo sapiens

<400> SEQUENCE: 6
atggacgaga gaccaagaa agcagaggaa atggccctga gcctcacccg agcagtggcg     60
ggcggggatg aacaggtggc aatgaagtgt gccatctggc tggcagagca acgggtgccc   120
ctgagtgtgc aactgaagcc tgaggtctcc ccaacgcagg acatcaggct gtgggtgagc   180
gtggaggatg ctcagatgca caccgtcacc atctggctca gtgcgccc tgatatgaca    240 gtggcgtctc tcaaggacat ggttttctg gactatggct tcccaccagt cttgcagcag   300
tgggtgattg ggcagcggct ggcacgagac caggagaccc tgcactccca tggggtgcgg   360
cagaatgggg acagtgccta cctctatctg ctgtcagccc gcaacaccatc cctcaaccct   420 caggagctgc agcgggagcg gcagctgcgg atgctggaag atctgggctt caaggacctc   480
acgctgcagc cgcggggccc tctggagcca ggccccccaa agcccggggt ccccaggaa    540 cccggacggg ggcagccaga tgcagtgcct gagtga                              576

<210> SEQ ID NO 7
<211> LENGTH: 599
<212> TYPE: PRT
<213> ORGANISM: Homo sapiens

<400> SEQUENCE: 7

Gly Asp Pro Glu Lys Gln Arg Gln Asp Lys Met Arg Glu Glu Gly Leu
1               5                   10                  15

Gln Leu Val Ser Met Ile Arg Glu Gly Glu Ala Ala Gly Ala Cys Pro
            20                  25                  30

Glu Glu Ile Phe Ser Ala Leu Gln Tyr Ser Gly Thr Glu Val Pro Leu
        35                  40                  45

Gln Trp Leu Arg Ser Glu Leu Pro Tyr Val Leu Glu Met Val Ala Glu
    50                  55                  60

Leu Ala Gly Gln Gln Asp Pro Gly Leu Gly Ala Phe Ser Cys Gln Glu
65                  70                  75                  80

Ala Arg Arg Ala Trp Leu Asp Arg His Gly Asn Leu Asp Glu Ala Val
                85                  90                  95

Glu Glu Cys Val Arg Thr Arg Arg Lys Val Gln Glu Leu Gln Ser
            100                 105                 110

Leu Gly Phe Gly Pro Glu Glu Gly Ser Leu Gln Ala Leu Phe Gln His

```
                115                 120                 125
Gly Gly Asp Val Ser Arg Ala Leu Thr Glu Leu Gln Arg Gln Arg Leu
    130                 135                 140

Glu Pro Phe Arg Gln Arg Leu Trp Asp Ser Gly Pro Glu Pro Thr Pro
145                 150                 155                 160

Ser Trp Asp Gly Pro Asp Lys Gln Ser Leu Val Arg Arg Leu Leu Ala
                165                 170                 175

Val Tyr Ala Leu Pro Ser Trp Gly Arg Ala Glu Leu Ala Leu Ser Leu
                180                 185                 190

Leu Gln Glu Thr Pro Arg Asn Tyr Glu Leu Gly Asp Val Val Glu Ala
                195                 200                 205

Val Arg His Ser Gln Asp Arg Ala Phe Leu Arg Arg Leu Leu Ala Gln
    210                 215                 220

Glu Cys Ala Val Cys Gly Trp Ala Leu Pro His Asn Arg Met Gln Ala
225                 230                 235                 240

Leu Thr Ser Cys Glu Cys Thr Ile Cys Pro Asp Cys Phe Arg Gln His
                245                 250                 255

Phe Thr Ile Ala Leu Lys Glu Lys His Ile Thr Asp Met Val Cys Pro
                260                 265                 270

Ala Cys Gly Arg Pro Asp Leu Thr Asp Thr Gln Leu Leu Ser Tyr
                275                 280                 285

Phe Ser Thr Leu Asp Ile Gln Leu Arg Glu Ser Glu Pro Asp Ala
                290                 295                 300

Tyr Ala Leu Phe His Lys Lys Leu Thr Glu Gly Val Leu Met Arg Asp
305                 310                 315                 320

Pro Lys Phe Leu Trp Cys Ala Gln Cys Ser Phe Gly Phe Ile Tyr Glu
                325                 330                 335

Arg Glu Gln Leu Glu Ala Thr Cys Pro Gln Cys His Gln Thr Phe Cys
                340                 345                 350

Val Arg Cys Lys Arg Gln Trp Glu Glu Gln His Arg Gly Arg Ser Cys
                355                 360                 365

Glu Asp Phe Gln Asn Trp Lys Arg Met Asn Asp Pro Glu Tyr Gln Ala
    370                 375                 380

Gln Gly Leu Ala Met Tyr Leu Gln Glu Asn Gly Ile Asp Cys Pro Lys
385                 390                 395                 400

Cys Lys Phe Ser Tyr Ala Leu Ala Arg Gly Gly Cys Met His Phe His
                405                 410                 415

Cys Thr Gln Cys Arg His Gln Phe Cys Ser Gly Cys Tyr Asn Ala Phe
                420                 425                 430

Tyr Ala Lys Asn Lys Cys Pro Glu Pro Asn Cys Arg Val Lys Lys Ser
                435                 440                 445

Leu His Gly His His Pro Arg Asp Cys Leu Phe Tyr Leu Arg Asp Trp
    450                 455                 460

Thr Ala Leu Arg Leu Gln Lys Leu Leu Gln Asp Asn Asn Val Met Phe
465                 470                 475                 480

Asn Thr Glu Pro Pro Ala Gly Ala Arg Ala Val Pro Gly Gly Gly Cys
                485                 490                 495

Arg Val Ile Glu Gln Lys Glu Val Pro Asn Gly Leu Arg Asp Glu Ala
                500                 505                 510

Cys Gly Lys Glu Thr Pro Ala Gly Tyr Ala Gly Leu Cys Gln Ala His
                515                 520                 525

Tyr Lys Glu Tyr Leu Val Ser Leu Ile Asn Ala His Ser Leu Asp Pro
                530                 535                 540
```

```
Ala Thr Leu Tyr Glu Val Glu Glu Leu Glu Thr Ala Thr Glu Arg Tyr
545                 550                 555                 560

Leu His Val Arg Pro Gln Pro Leu Ala Gly Glu Asp Pro Pro Ala Tyr
                565                 570                 575

Gln Ala Arg Leu Leu Gln Lys Leu Thr Glu Glu Val Pro Leu Gly Gln
            580                 585                 590

Ser Ile Pro Arg Arg Lys
        595

<210> SEQ ID NO 8
<211> LENGTH: 1800
<212> TYPE: DNA
<213> ORGANISM: Homo sapiens

<400> SEQUENCE: 8
ggagatcctg agaagcagcg ccaagacaag atgcgggaag aaggcctcca gctagtgagc      60
atgatccggg aagggaagc cgcaggtgcc tgtccagagg atcttctc ggctctgcag        120 tactcgggca ctgaggtgcc tctgcagtgg ttgcgctcag aactgcccta cgtcctggag    180
atggtggctg agctggctgg acagcaggac cctgggctgg gtgccttttc ctgtcaggag    240
gcccggagag cctggctgga tcgtcatggc aaccttgatg aagctgtgga ggagtgtgtg    300
aggaccaggc gaaggaaggt gcaggagctc cagtctctag ctttgggcc tgaggagggg     360 tctctccagg cattgttcca gcacggaggt gatgtgtcac gggccctgac tgagctacag    420
cgccaacgcc tagagccctt ccgccagcgc tctgggaca gtggccctga gcccacccct     480
tcctgggatg ggccagacaa gcagagcctg gtcaggcggc ttttggcagt ctacgcactc    540
cccagctggg gccgggcaga gctggcactg tcactgctgc aggagacacc caggaactat    600
gagttggggg atgtggtaga agctgtgagg cacagccagg accgggcctt cctgcgccgc    660
ttgcttgccc aggagtgtgc cgtgtgtggc tgggccctgc ccacaaccg gatgcaggcc    720 ctgacttcct gtgagtgcac catctgtcct gactgcttcc gccagcactt caccatcgcc   780
ttgaaggaga agcacatcac agacatggtg tgccctgcct gtggccgccc cgacctcacc   840
gatgacacac agttgctcag ctacttctct acccttgaca tccagcttcg cgagagccta   900
gagccagatg cctatgcgtt gttccataag aagctgaccg agggtgtgct gatgcgggac    960
cccaagttct gtggtgtgc ccagtgctcc tttggcttca tatatgagcg tgagcagctg  1020
gaggcaactt gtccccagtg tcaccagacc ttctgtgtgc gctgcaagcg ccagtgggag  1080
gagcagcacc gaggtcggag ctgtgaggac ttccagaact ggaaacgcat gaacgaccca  1140
gaataccagg cccagggcct agcaatgtat cttcaggaaa acggcattga ctgccccaaa  1200
tgcaagttct cgtacgccct ggcccgagga ggctgcatgc actttcactg tacccagtgc  1260
cgccaccagt tctgcagcgg ctgctacaat gcctttacg ccaagaataa atgtccagag  1320
cctaactgca gggtgaaaaa gtccctgcac ggccaccacc ctcgagactg cctcttctac  1380
ctgcgggact ggactgctct ccggcttcag aagctgctac aggacaataa cgtcatgttt  1440
aatacagagc ctccagctgg ggcccgggca gtccctggag cggctgccg agtgatagag  1500 cagaaggagg ttcccaatgg gctcagggac gaagcttgtg caaggaaac tccagctggc  1560 tatgccggcc tgtgccaggc acactacaaa gagtatcttg tgagcctcat caatgcccac  1620
tcgctggacc cagccacctt gtatgaggtg aaagagctgg agacggccac tgagcgctac  1680
ctgcacgtac gccccagcc tttggctgga ggagatcccc ctgcttacca ggcccgcttg  1740
ttacagaagc tgacagaaga ggtacccttg ggacagagta tccccgcag gcggaagtag  1800
```

<210> SEQ ID NO 9
<211> LENGTH: 22
<212> TYPE: PRT
<213> ORGANISM: Artificial Sequence
<220> FEATURE:
<223> OTHER INFORMATION: Tag Sequence

<400> SEQUENCE: 9

```
Met Arg Gly Ser His His His His His Ser Gln Asp Pro Asn Ser
1               5                   10                  15

Glu Asn Leu Tyr Phe Gln
            20
```

<210> SEQ ID NO 10
<211> LENGTH: 387
<212> TYPE: PRT
<213> ORGANISM: Homo sapiens

<400> SEQUENCE: 10

```
Met Ala Pro Pro Ala Gly Gly Ala Ala Ala Ala Ser Asp Leu Gly
1               5                   10                  15

Ser Ala Ala Val Leu Leu Ala Val His Ala Ala Val Arg Pro Leu Gly
            20                  25                  30

Ala Gly Pro Asp Ala Glu Ala Gln Leu Arg Arg Leu Gln Leu Ser Ala
            35                  40                  45

Asp Pro Glu Arg Pro Gly Arg Phe Arg Leu Glu Leu Leu Gly Ala Gly
    50                  55                  60

Pro Gly Ala Val Asn Leu Glu Trp Pro Leu Glu Ser Val Ser Tyr Thr
65                  70                  75                  80

Ile Arg Gly Pro Thr Gln His Glu Leu Gln Pro Pro Gly Gly Pro
            85                  90                  95

Gly Thr Leu Ser Leu His Phe Leu Asn Pro Gln Glu Ala Gln Arg Trp
            100                 105                 110

Ala Val Leu Val Arg Gly Ala Thr Val Glu Gly Gln Asn Gly Ser Lys
            115                 120                 125

Ser Asn Ser Pro Pro Ala Leu Gly Pro Glu Ala Cys Pro Val Ser Leu
            130                 135                 140

Pro Ser Pro Pro Glu Ala Ser Thr Leu Lys Gly Pro Pro Pro Glu Ala
145                 150                 155                 160

Asp Leu Pro Arg Ser Pro Gly Asn Leu Thr Glu Arg Glu Glu Leu Ala
                165                 170                 175

Gly Ser Leu Ala Arg Ala Ile Ala Gly Gly Asp Glu Lys Gly Ala Ala
            180                 185                 190

Gln Val Ala Ala Val Leu Ala Gln His Arg Val Ala Leu Ser Val Gln
            195                 200                 205

Leu Gln Glu Ala Cys Phe Pro Pro Gly Pro Ile Arg Leu Gln Val Thr
    210                 215                 220

Leu Glu Asp Ala Ala Ser Ala Ala Ser Ala Ala Ser Ala His Val
225                 230                 235                 240

Ala Leu Gln Val His Pro His Cys Thr Val Ala Ala Leu Gln Glu Gln
                245                 250                 255

Val Phe Ser Glu Leu Gly Phe Pro Pro Ala Val Gln Arg Trp Val Ile
            260                 265                 270

Gly Arg Cys Leu Cys Val Pro Glu Arg Ser Leu Ala Ser Tyr Gly Val
            275                 280                 285

Arg Gln Asp Gly Asp Pro Ala Phe Leu Tyr Leu Leu Ser Ala Pro Arg
    290                 295                 300
```

```
Glu Ala Pro Ala Thr Gly Pro Ser Pro Gln His Pro Gln Lys Met Asp
305                 310                 315                 320

Gly Glu Leu Gly Arg Leu Phe Pro Pro Ser Leu Gly Leu Pro Pro Gly
                325                 330                 335

Pro Gln Pro Ala Ala Ser Ser Leu Pro Ser Pro Leu Gln Pro Ser Trp
            340                 345                 350

Ser Cys Pro Ser Cys Thr Phe Ile Asn Ala Pro Asp Arg Pro Gly Cys
        355                 360                 365

Glu Met Cys Ser Thr Gln Arg Pro Cys Thr Trp Asp Pro Leu Ala Ala
    370                 375                 380

Ala Ser Thr
385

<210> SEQ ID NO 11
<211> LENGTH: 1164
<212> TYPE: DNA
<213> ORGANISM: Homo sapiens

<400> SEQUENCE: 11
atggcgccgc cagcgggcgg ggcggcggcg gcggcctcgg acttgggctc cgccgcagtg    60
ctcttggctg tgcacgccgc ggtgaggccg ctgggcgccg gccagacgc cgaggcacag    120 ctgcggaggc tgcagctgag cgcggaccct gagaggcctg gcgcttccg gctggagctg    180 ctgggcgcgg gacctggggc ggttaatttg gagtggcccc tggagtcagt ttcctacacc    240
atccgaggcc ccacccagca cgagctacag cctccaccag gagggcctgg aaccctcagc    300
ctgcacttcc tcaaccctca ggaagctcag cggtgggcag tcctagtccg aggtgccacc    360
gtggaaggac agaatggcag caagagcaac tcaccaccag ccttgggccc agaagcatgc    420
cctgtctccc tgcccagtcc cccggaagcc tccacactca agggccctcc acctgaggca    480
gatcttccta ggagccctgg aaacttgacg gagagagaag agctggcagg agcctggcc    540 cgggctattg caggtggaga cgagaagggg gcagcccaag tggcagccgt cctggcccag    600
catcgtgtgg ccctgagtgt tcagcttcag gaggcctgct tcccacctgg ccccatcagg    660
ctgcaggtca cacttgaaga cgctgcctct gccgcatccg ccgcgtcctc tgcacacgtt    720
gccctgcagg tccaccccca ctgcactgtt gcagctctcc aggagcaggt gttctcagag    780
ctcggtttcc cgccagccgt gcaacgctgg gtcatcggac ggtgcctgtg tgtgcctgag    840
cgcagccttg cctcttacgg ggttcggcag gatggggacc ctgctttcct ctacttgctg    900
tcagctcctc gagaagcccc agccacagga cctagccctc agcaccccca gaagatggac    960
ggggaacttg gacgcttgtt tcccccatca ttggggctac ccccaggccc ccagccagct   1020
gcctccagcc tgcccagtcc actccagccc agctggtcct gtccttcctg caccttcatc   1080
aatgccccag accgccctgg ctgtgagatg tgtagcaccc agaggccctg cacttgggac   1140 cccttgctg cagcttccac ctag                                          1164

<210> SEQ ID NO 12
<211> LENGTH: 176
<212> TYPE: PRT
<213> ORGANISM: Homo sapiens

<400> SEQUENCE: 12

Met Arg Glu Glu Leu Ala Gly Ser Leu Ala Arg Ala Ile Ala Gly Gly
1               5                   10                  15

Asp Glu Lys Gly Ala Ala Gln Val Ala Ala Val Leu Ala Gln His Arg
            20                  25                  30
```

```
Val Ala Leu Ser Val Gln Leu Gln Glu Ala Cys Phe Pro Pro Gly Pro
            35                  40                  45

Ile Arg Leu Gln Val Thr Leu Glu Asp Ala Ala Ser Ala Ala Ser Ala
    50                  55                  60

Ala Ser Ser Ala His Val Ala Leu Gln Val His Pro His Cys Thr Val
65                  70                  75                  80

Ala Ala Leu Gln Glu Gln Val Phe Ser Glu Leu Gly Phe Pro Pro Ala
                85                  90                  95

Val Gln Arg Trp Val Ile Gly Arg Cys Leu Cys Val Pro Glu Arg Ser
               100                 105                 110

Leu Ala Ser Tyr Gly Val Arg Gln Asp Gly Asp Pro Ala Phe Leu Tyr
           115                 120                 125

Leu Leu Ser Ala Pro Arg Glu Ala Pro Ala Thr Gly Pro Ser Pro Gln
        130                 135                 140

His Pro Gln Lys Met Asp Gly Glu Leu Gly Arg Leu Phe Pro Pro Ser
145                 150                 155                 160

Leu Gly Leu Pro Pro Gly Pro Gln Pro Ala Ala Ser Ser Leu Pro Ser
                165                 170                 175

<210> SEQ ID NO 13
<211> LENGTH: 531
<212> TYPE: DNA
<213> ORGANISM: Homo sapiens

<400> SEQUENCE: 13
atgagagaag agctggcagg gagcctggcc cgggctattg caggtggaga cgagaagggg        60
gcagcccaag tggcagccgt cctggcccag catcgtgtgg ccctgagtgt tcagcttcag       120
gaggcctgct tcccacctgg ccccatcagg ctgcaggtca cacttgaaga cgctgcctct       180
gccgcatccg ccgcgtcctc tgcacacgtt gccctgcagg tccaccccca ctgcactgtt       240
gcagctctcc aggagcaggt gttctcagag ctcggtttcc cgccagccgt gcaacgctgg       300
gtcatcggac ggtgcctgtg tgtgcctgag cgcagccttg cctcttacgg ggttcggcag       360 gatgggacc ctgctttcct ctacttgctg tcagctcctc gagaagcccc agccacagga        420
cctagccctc agcaccccca gaagatggac ggggaacttg gacgcttgtt tcccccatca       480
ttggggctac cccaggccc ccagccagct gcctccagcc tgcccagttg a                 531
```

UBIQUITIN LIGASE AND USE THEREOF

This application is a U.S. national stage of International Application No. PCT/JP2010/063345 filed Aug. 6, 2010.

TECHNICAL FIELD

The present invention relates to a novel ubiquitin ligase and use thereof. In particular, the present invention relates to a novel ubiquitin ligase comprising a complex of plural proteins, an expression vector for a constituent protein of the ubiquitin ligase, a transformant with the expression vector, and a screening method for inhibitors of linear polyubiquitination, the method using the ubiquitin ligase.

BACKGROUND ART

The ubiquitin conjugation system is a posttranslational modification system. By the function of three kinds of enzymes, a ubiquitin activating enzyme (E1), a ubiquitin conjugating enzyme (E2) and a ubiquitin ligase (E3), the ubiquitin system conjugates polyubiquitin chains, polymer of ubiquitin, to substrate proteins selectively recognized by E3s and regulates their functions. Although it was originally considered that all polyubiquitinated proteins are led to degradation, the concept of polyubiquitination has been broadened and it is currently understood that polyubiquitination regulates protein functions in various manners. Various polyubiquitin chains with different linkage of ubiquitins are present in the living body, and it is being proved that the regulatory mechanism for polyubiquitinated proteins varies with the kind of the polyubiquitin chain. It has been conventionally considered that polyubiquitin chains are assembled by formation of isopeptide bonds via lysine residues of ubiquitins. In such circumstances, the present inventor is the first in the world to show assembly of a linear polyubiquitin chain via N-terminal methionine, and involvement of the linear polyubiquitination in NF-κB activation.

Specifically, the present inventor found out that a complex of HOIL-1L and HOIP is a ubiquitin ligase which mediates assembly of a linear polyubiquitin chain, and named the complex LUBAC (linear ubiquitin chain assemble complex) (see Non Patent Literature 1). Further, the present inventor clarified that the LUBAC ubiquitin ligase is involved in the classical pathway of NF-κB activation in that the LUBAC ubiquitin ligase mediates linear ubiquitination of NEMO (NF-κB essential modulator), a component of the IKK (IκB kinase) complex, which leads to IKK activation and selective activation of NF-κB (see Non Patent Literature 2).

Furthermore, the present inventor found out that Sharpin is also a constituent of the ubiquitin ligase for mediating assembly of a linear polyubiquitin chain. Accordingly, the present inventor decided to refer to, as LUBAC, a ubiquitin ligase complex composed of the three proteins, namely Sharpin, HOIL-1L and HOIP, or composed of two proteins, namely HOIL-1L and HOIP, or Sharpin and HOIP. Regarding Sharpin, it is reported that mice with spontaneous mutation of Sharpin, which are called cpdm mice, present with immune system disorders and the like including chronic dermatitis and absence of Peyer's patches (see Non Patent Literature 3).

CITATION LIST

Non Patent Literature

Non Patent Literature 1:
Kirisako, T. et al. A ubiquitin ligase complex assembles linear polyubiquitin chains. EMBO J., 25. 4877-4887 (2006)
Non Patent Literature 2:
Tokunaga, F. et al. Involvement of linear polyubiquitylation of NEMO in NF-κB activation. Nature Cell Biol., 11. 123-132 (2009)
Non Patent Literature 3:
Seymour, R. E. et al. Spontaneous mutations in the mouse Sharpin gene result in multiorgan inflammation, immune system dysregulation and dermatitis. Genes Immun., 8. 416-421 (2007)

SUMMARY OF INVENTION

Technical Problem

The present inventor has been attempting to establish a LUBAC expression system that enables efficient expression of a recombinant LUBAC, but has not yet succeeded. Accordingly, an object of the present invention is to provide a novel ubiquitin ligase which has linear polyubiquitination activity and can be efficiently expressed and purified, an expression vector for a constituent protein of the ubiquitin ligase, a transformant with the expression vector, and a screening method for inhibitors of linear polyubiquitination, the method using the ubiquitin ligase.

Solution to Problem

The present invention includes the following as a solution to the above-mentioned problems.
[1] A ubiquitin ligase comprising a complex of the following (a) and (b).
(a) A protein having a part of HOIP and at least having a UBA region and a RING-IBR-RING region thereof
(b) One or more kinds of proteins which individually form a complex with the above (a)
[2] The ubiquitin ligase according to the above [1], wherein the above (b) is a protein having a region capable of binding to the UBA region of HOIP.
[3] The ubiquitin ligase according to the above [2], wherein the above (b) is the following (1) and/or (2).
(1) HOIL-1L, or a protein having a part of HOIL-1L and at least having a UBL region thereof
(2) Sharpin, or a protein having a part of Sharpin and at least having a UBL region thereof
[4] The ubiquitin ligase according to the above [3], wherein the above (1) is a protein having the amino acid sequence represented by SEQ ID NO: 5, or a protein having an amino acid sequence the same as the amino acid sequence represented by SEQ ID NO: 5 except for having deletion, substitution or addition of one to several amino acids, and
wherein the above (2) is a protein having the amino acid sequence represented by SEQ ID NO: 12, or a protein having an amino acid sequence the same as the amino acid sequence represented by SEQ ID NO: 12 except for having deletion, substitution or addition of one to several amino acids.
[5] The ubiquitin ligase according to the above [1], wherein the above (a) is a protein having the amino acid sequence represented by SEQ ID NO: 7, or a protein having an amino acid sequence the same as the amino acid sequence represented by SEQ ID NO: 7 except for having deletion, substitution or addition of one to several amino acids.

[6] An expression vector containing a polynucleotide encoding the following (A) and/or (B).

(A) A protein which has a part of HOIP and at least has a UBA region and a RING-IBR-RING region thereof and which forms, with the following (B), a complex exhibiting ubiquitin ligase activity (B) One or more kinds of proteins which individually form, with the above (A), a complex exhibiting ubiquitin ligase activity

[7] The expression vector according to the above [6], wherein the above (B) is a protein which has a region capable of binding to the UBA region of HOIP and which forms, with the above (A), a complex exhibiting ubiquitin ligase activity.

[8] The expression vector according to the above [7], wherein the above (B) is the following (I) and/or (II).

(I) HOIL-1L, or a protein which has a part of HOIL-1L and at least has a UBL region thereof and which forms, with the above (A), a complex exhibiting ubiquitin ligase activity (II) Sharpin, or a protein which has a part of Sharpin and at least has a UBL region thereof and which forms, with the above (A), a complex exhibiting ubiquitin ligase activity

[9] The expression vector according to the above [8], wherein the above (I) is a protein having the amino acid sequence represented by SEQ ID NO: 5, or a protein which has an amino acid sequence the same as the amino acid sequence represented by SEQ ID NO: 5 except for having deletion, substitution or addition of one to several amino acids and which forms, with the above (A), a complex exhibiting ubiquitin ligase activity, and wherein the above (II) is a protein having the amino acid sequence represented by SEQ ID NO: 12, or a protein which has an amino acid sequence the same as the amino acid sequence represented by SEQ ID NO: 12 except for having deletion, substitution or addition of one to several amino acids and which forms, with the above (A), a complex exhibiting ubiquitin ligase activity.

[10] The expression vector according to the above [6], wherein the above (A) is a protein having the amino acid sequence represented by SEQ ID NO: 7, or a protein which has an amino acid sequence the same as the amino acid sequence represented by SEQ ID NO: 7 except for having deletion, substitution or addition of one to several amino acids and which forms, with the above (B), a complex exhibiting ubiquitin ligase activity.

[11] The expression vector according to the above [9], wherein the above (I) is encoded by a polynucleotide having the base sequence represented by SEQ ID NO: 6, or a polynucleotide which hybridizes with a polynucleotide having a base sequence complementary to the base sequence represented by SEQ ID NO: 6 under stringent conditions and which encodes a protein which forms, with the above (A), a complex exhibiting ubiquitin ligase activity, and wherein the above (II) is encoded by a polynucleotide having the base sequence represented by SEQ ID NO: 13, or a polynucleotide which hybridizes with a polynucleotide having a base sequence complementary to the base sequence represented by SEQ ID NO: 13 under stringent conditions and which encodes a protein which forms, with the above (A), a complex exhibiting ubiquitin ligase activity.

[12] The expression vector according to the above [10], wherein the above (A) is encoded by a polynucleotide having the base sequence represented by SEQ ID NO: 8, or a polynucleotide which hybridizes with a polynucleotide having a base sequence complementary to the base sequence represented by SEQ ID NO: 8 under stringent conditions and which encodes a protein which forms, with the above (B), a complex exhibiting ubiquitin ligase activity.

[13] A transformant with the expression vector according to any of the above [6] to [12].

[14] A screening method for inhibitors of linear polyubiquitination, the method comprising the steps of: bringing a test substance into contact with the ubiquitin ligase according to any of the above [1] to [5], measuring the activity level of the ubiquitin ligase, and comparing the above activity level to the activity level of the ubiquitin ligase not brought into contact with the test substance.

Advantageous Effects of Invention

According to the present invention, a novel ubiquitin ligase can be provided. In addition, an expression vector for a constituent protein of the ubiquitin ligase and a transformant with the expression vector can also be provided. Use of the expression vector and the transformant of the present invention enables efficient expression and high-yield purification of the ubiquitin ligase of the present invention. By use of the ubiquitin ligase of the present invention, a screening method for inhibitors of linear polyubiquitination can also be provided. The screening method enables selection of substances that selectively inhibit NF-κB activation, and therefore the selected inhibitors can be active ingredient candidates for preventive or therapeutic medicaments for various NF-κB-associated diseases.

DESCRIPTION OF EMBODIMENTS

[LUBAC]

Figure 1A:
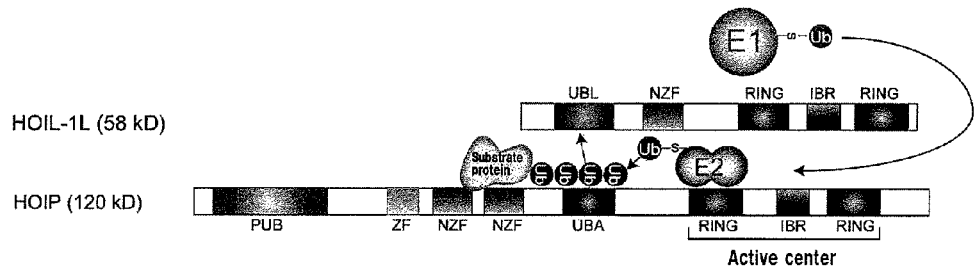
FIG. 1(a) is an explanatory diagram showing the structure of LUBAC composed of HOIL-1L and HOIP and the mechanism of LUBAC-mediated linear ubiquitination.

LUBAC (linear ubiquitin chain assemble complex) is a ubiquitin ligase, which the present inventor discovered. As shown in FIGS. 1(a), (b) and (c), LUBAC is a ubiquitin ligase complex composed of three proteins, namely HOIL-1L, HOIP and Sharpin, or composed of two proteins, namely HOIL-1L and HOIP, or Sharpin and HOIP. LUBAC has the activity of assembling a linear polyubiquitin chain.

HOIL-1L is a splicing isoform of HOIL-1 (heme-oxidized IRP2 ligase-1), which has a longer N-terminal sequence compared to HOIL-1, and was discovered as predominant intracellular HOIL-1. As shown in FIG. 1(a), HOIL-1L is a 58-kD protein having a UBL domain (UBL), a Npl4 zinc finger domain (NZF) and a RING-IBR-RING domain in this order from the N-terminus. HOIL-1L is a protein having the amino acid sequence represented by SEQ ID NO: 1, and the base sequence of the HOIL-1L-encoding gene is represented by SEQ ID NO: 2. HOIL-1L is also called RBCK1 or RNF54. The base sequence of the HOIL-1L-encoding gene (RBCK1, transcript variant 2) is registered with DDBJ/GenBank/EMBL as accession number: NM_031229.

HOIP (HOIL-1L-interacting protein) was identified as a HOIL-1L-associating protein. As shown in FIG. 1(a), HOIP is a 120-kD protein having a PUB domain (PUB) capable of binding to p97/VCP in the N-terminal region, followed by three zinc finger domains (ZF, NZF and NZF), a UBA domain (UBA) and a RING-IBR-RING domain. HOIP is a protein having the amino acid sequence represented by SEQ ID NO: 3, and the base sequence of the HOIP-encoding gene is represented by SEQ ID NO: 4. HOIP is also called RNF31. The base sequence of the HOIP-encoding gene is registered with DDBJ/GenBank/EMBL as accession number: AB265810.

HOIL-1L and HOIP are considered to form a complex and exist as an oligomer in cells. The present inventor found out that a HOIL-1L-HOIP complex has such a ubiquitin ligase activity as to mediate assembly of a linear polyubiquitin chain via N-terminal methionine, not assembly of a polyubiquitin chain by formation of isopeptide bonds via lysine residues of ubiquitins as conventionally known (Non Patent Literature 1).

Figure 1B:
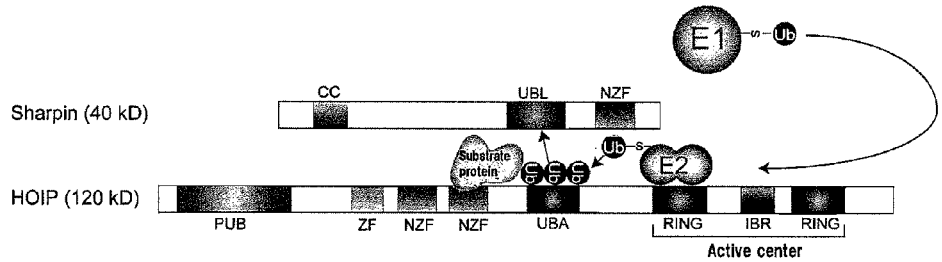
FIG. 1(b) is an explanatory diagram showing the structure of LUBAC composed of Sharpin and HOIP and the mechanism of LUBAC-mediated linear ubiquitination.

Furthermore, the present inventor found out that Sharpin (SHANK-associated RH domain-interacting protein) is also a constituent of the ubiquitin ligase for mediating assembly of a linear polyubiquitin chain. In other words, a HOIL-1L-Sharpin-HOIP complex (see FIG. 1(c)) and a Sharpin-HOIP complex (see FIG. 1(b)) each have such a ubiquitin ligase activity as to mediate assembly of a linear polyubiquitin chain via N-terminal methionine, not assembly of a polyubiquitin chain by formation of isopeptide bonds via lysine residues of ubiquitins as conventionally known. As shown in FIGS. 1(b) and (c), Sharpin is a 40-kD protein having a coiled-coil domain (CC), a UBL domain (UBL), a Npl4 zinc finger domain (NZF) and a RING-IBR-RING domain in this order from the N-terminus. Sharpin is a protein having the amino acid sequence represented by SEQ ID NO: 10, and the base sequence of the Sharpin-encoding gene is represented by SEQ ID NO: 11. The base sequence of the Sharpin-encoding gene is registered with DDBJ/GenBank/EMBL as accession number: FJ655995.

Figure 1C:
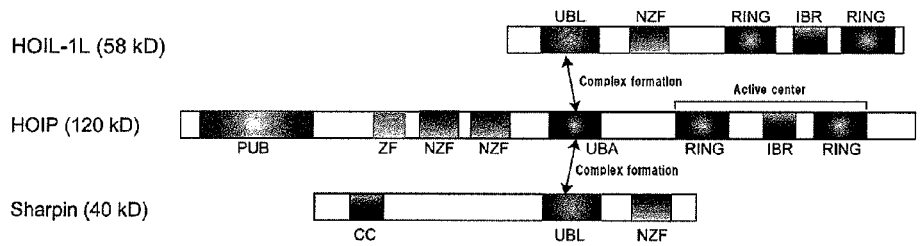
FIG. 1(c) shows the structure of LUBAC composed of three components, namely HOIL-1L, Sharpin and HOIP.

As shown in FIG. 1(c), HOIL-1L, Sharpin and HOIP can form a tertiary-protein complex. The present inventor also found out that, in the living body, the tertiary-protein complex is stably present while a complex of HOIL-1L and HOIP and a complex of Sharpin and HOIP are unstable.

[LUBAC-Mediated Selective NF-κB Activation Mechanism]

NF-κB is a transcription factor that can be activated by various stimuli. It is known that NF-κB is associated with cell growth, inflammation, immune response, etc., and that its activity is increased in various cancers including multiple myeloma. Therefore, selective inhibition of NF-κB activation is thought to be an excellent target for medicaments for rheumatoid/allergic diseases and cancers.

Figure 2:
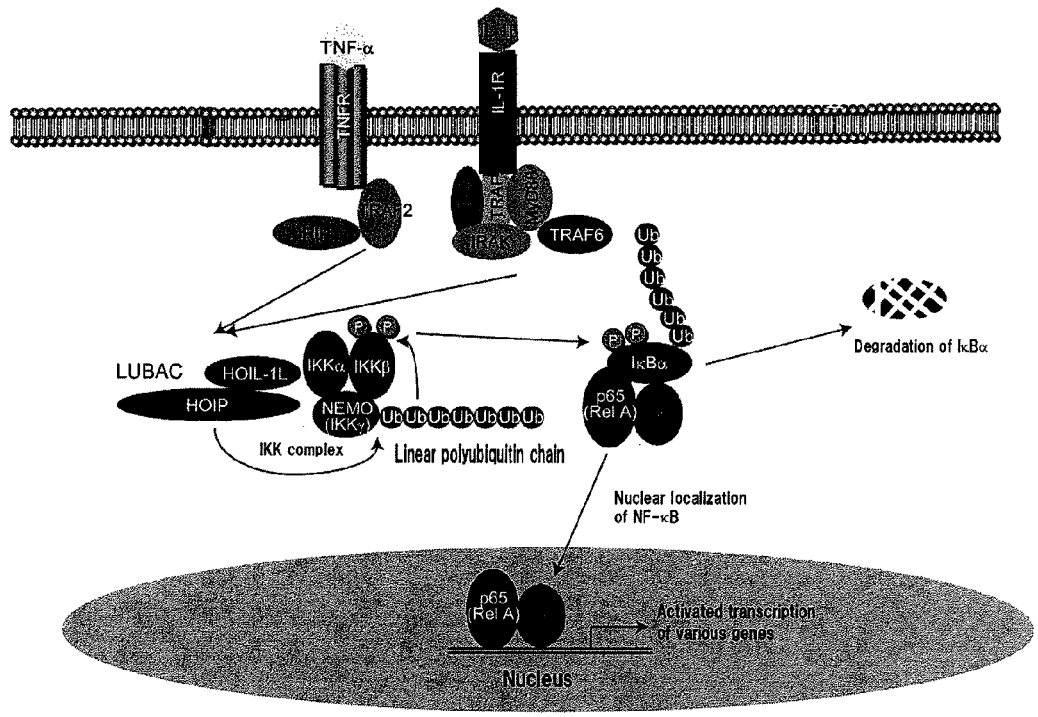
FIG. 2 shows a schematic view of the LUBAC-mediated NF-κB activation mechanism.

The schematic view of the NF-κB activation mechanism mediated by LUBAC composed of HOIL-1L and HOIP is shown in FIG. 2. The same mechanism is true in the NF-κB activation mediated by LUBAC composed of Sharpin and HOIP, or by LUBAC composed of HOIL-1L, Sharpin and HOIP. As shown in FIG. 2, NF-κB is a hetero-dimeric transcription factor and is present in the cytoplasm in a bound form with an inhibitory protein, IκBα in the absence of stimulation. Activation of the IKK complex by various stimuli results in phosphorylation of IκBα and subsequent degradation thereof. NF-κB released from IκBα enters into the nucleus and activates transcription of various genes. Thus, for understanding of signal-dependent NF-κB activation, the elucidation of stimulation-dependent IKK complex activation mechanism is indispensable, and many studies have been done for this purpose. In the current situation, the conventional dogma is collapsing and consensus has not been reached yet.

The present inventor clarified that the LUBAC ubiquitin ligase selectively binds, in a stimulation (e.g. TNF-α)-dependent manner, to NEMO serving as an IKK complex subunit for activity regulation, and then mediates linear polyubiquitination of NEMO, leading to IKK complex activation, followed by NF-κB activation (Non Patent Literature 2). From the research results so far, it seems that the LUBAC-mediated linear polyubiquitination of NEMO selectively activates NF-κB.

[Novel Ubiquitin Ligase]

The ubiquitin ligase of the present invention at least comprises a complex of the following (a) and (b).

(a) A protein having a part of HOIP and at least having a UBA region and a RING-IBR-RING region thereof (b) One or more kinds of proteins which individually form a complex with the above (a)

The above (b) is not particularly limited as long as it forms, with the above (a), a protein complex exhibiting ubiquitin ligase activity. The above (b) may be two or more kinds of proteins, and therefore, the ubiquitin ligase of the present invention may be a complex of three or more kinds of proteins including the above (a). For example, preferred as the above (b) is a protein having a region capable of binding to the UBA region of HOIP. More preferred is, for example, (1) HOIL-1L, or a protein having a part of HOIL-1L and at least having a UBL region thereof, or (2) Sharpin, or a protein having a part of Sharpin and at least having a UBL region thereof.

The ubiquitin ligase of the present invention more preferably comprises a complex of (a) and (1), a complex of (a) and (2), or a complex of (a), (1) and (2).

The full-length HOIL-1L is a protein having the amino acid sequence represented by SEQ ID NO: 1 as described above, and the UBL region corresponds to a region of residues 70 to 130 of SEQ ID NO: 1. Therefore, in the case where the above (1) is HOIL-1L, a protein having the amino acid sequence represented by SEQ ID NO: 1 can be used. In the case where the above (1) is a protein having a part of HOIL-1L and at least having a UBL region thereof, namely a partial HOIL-1L protein having a UBL region of HOIL-1L, a protein having not the full length of the amino acid sequence represented by SEQ ID NO: 1, but at least a region of residues 70 to 130 thereof can be used. Preferred is a partial HOIL-1L protein having no Npl4 zinc finger domain (NZF), and more preferred is a partial HOIL-1L protein having neither NZF nor a RING-IBR-RING domain (see FIG. 1(a)).

As used herein, HOIL-1L is not limited to a protein having the amino acid sequence represented by SEQ ID NO: 1, and may be a mutant of HOIL-1L as long as the mutant forms, with HOIP, a complex exhibiting ubiquitin ligase activity. Such a mutant HOIL-1L or a partial protein thereof having a region corresponding to the UBL region of HOIL-1L is suitable as the protein of the above (b) (1) according to the present invention. The mutant HOIL-1L is, for example, a protein which has an amino acid sequence the same as the amino acid sequence represented by SEQ ID NO: 1 except for having deletion, substitution or addition of one to several amino acids and which forms, with HOIP, a complex exhibiting ubiquitin ligase activity. In addition, a protein having a region equivalent to the UBL region of HOIL-1L, or a partial protein thereof having such a UBL-equivalent region is suitable as the protein of the above (b).

Still more preferred as the protein of the above (b) (1) is a protein having the amino acid sequence represented by SEQ ID NO: 5. The amino acid sequence represented by SEQ ID NO: 5 corresponds to a region of residues 1 to 191 of SEQ ID NO: 1. Needless to say, a protein having an amino acid sequence the same as the amino acid sequence represented by SEQ ID NO: 5 except for having deletion, substitution or addition of one to several amino acids is also suitable as long as the protein forms, with the protein of the above (a), a complex exhibiting ubiquitin ligase activity.

The full-length Sharpin is a protein having the amino acid sequence represented by SEQ ID NO: 10 as described above, and the UBL region corresponds to a region of residues 240 to 300 of SEQ ID NO: 10. Therefore, in the case where the above (2) is Sharpin, a protein having the amino acid sequence represented by SEQ ID NO: 10 can be used. In the case where the above (2) is a protein having a part of Sharpin and at least having a UBL region thereof, namely a partial Sharpin protein having a UBL region of Sharpin, a protein having a part of the amino acid sequence represented by SEQ ID NO: 10 and at least having a region of residues 240 to 300 thereof can be used. Preferred is a partial Sharpin protein having no Npl4 zinc finger domain (NZF), and more preferred is a partial Sharpin protein having neither NZF nor a coiled-coil domain (CC) (see FIG. 1(b)).

As used herein, Sharpin is not limited to a protein having the amino acid sequence represented by SEQ ID NO: 10, and may be a mutant of Sharpin as long as the mutant forms, with HOIP, a complex exhibiting ubiquitin ligase activity. Such a mutant Sharpin or a partial protein thereof having a region corresponding to the UBL region of Sharpin is suitable as the protein of the above (b) (2) according to the present invention. The mutant Sharpin is, for example, a protein which has an amino acid sequence the same as the amino acid sequence represented by SEQ ID NO: 10 except for having deletion, substitution or addition of one to several amino acids and which forms, with HOIP, a complex exhibiting ubiquitin ligase activity. In addition, a protein having a region equivalent to the UBL region of Sharpin, or a partial protein thereof having such a UBL-equivalent region is suitable as the protein of the above (b).

Still more preferred as the protein of the above (b) (2) is a protein having the amino acid sequence represented by SEQ ID NO: 12. The amino acid sequence represented by SEQ ID NO: 12 corresponds to a region of residues 172 to 346 of SEQ ID NO: 10. Needless to say, a protein having an amino acid sequence the same as the amino acid sequence represented by SEQ ID NO: 12 except for having deletion, substitution or addition of one to several amino acids is also suitable as long as the protein forms, with the protein of the above (a), a complex exhibiting ubiquitin ligase activity.

The above (a) is not particularly limited as long as it is a protein having a part of HOIP and at least having a UBA region and a RING-IBR-RING region thereof. The full-length HOIP is a protein having the amino acid sequence represented by SEQ ID NO: 3 as described above, the UBA region corresponds to a region of residues 564 to 615 of SEQ ID NO: 3, the RING-IBR-RING region corresponds to a region of residues 699 to 901 of SEQ ID NO: 3, and the region from the N-terminus of the UBA region to the C-terminus of the RING-IBR-RING region corresponds to a region of residues 564 to 901 of SEQ ID NO: 3. Therefore, as the above (a), a protein having a part of the amino acid sequence represented by SEQ ID NO: 3 and at least having a region of residues 564 to 901 thereof can be used. Preferred is a partial HOIP protein having none of three zinc finger domains (ZF, NZF and NZF), and more preferred is a partial HOIP protein not having any of a PUB domain (PUB) and three zinc finger domains (ZF, NZF and NZF) (see FIGS. 1(a) and (b)).

As used herein, HOIP is not limited to a protein having the amino acid sequence represented by SEQ ID NO: 3, and may be a mutant of HOIP as long as the mutant forms, with HOIL-1L, a complex exhibiting ubiquitin ligase activity. A partial protein of such a mutant HOIP, as long as the partial protein has regions corresponding to the UBA region and the RING-IBR-RING region of HOIP, is suitable as the protein of the above (a) according to the present invention. The mutant HOIP is, for example, a protein which has an amino acid sequence the same as the amino acid sequence represented by SEQ ID NO: 3 except for having deletion, substitution or addition of one to several amino acids and which forms, with HOIL-1L, a complex exhibiting ubiquitin ligase activity.

Still more preferred as the protein of the above (a) is a protein having the amino acid sequence represented by SEQ ID NO: 7. The amino acid sequence represented by SEQ ID NO: 7 corresponds to a region of residues 474 to 1072 of SEQ ID NO: 3. Needless to say, a protein having an amino acid sequence the same as the amino acid sequence represented by SEQ ID NO: 7 except for having deletion, substitution or addition of one to several amino acids is also suitable as the protein of the above (a), as long as the protein forms, with the protein of the above (b), a complex exhibiting ubiquitin ligase activity.

As used herein, "having deletion, substitution or addition of one to several amino acids" means having deletion, substitution or addition of an amino acid(s), the number of which is in the range allowed by a known preparation method for mutant peptides, such as site-directed mutagenesis (preferably 10 or less, more preferably 7 or less, and even more preferably 5 or less). Such a mutant protein is not limited to a protein artificially mutated by a known preparation method for mutant polypeptides, and may be a protein isolated and purified from nature. It is well known in the art that modification to some amino acids in the amino acid sequence of a protein can be easily made without any significant effect on the structure or function of the protein. Aside from such artificial modification, it is also well known that there are natural mutants having no significant changes in the structure or function in comparison to wild-type proteins.

A preferable mutant has a conservative or non-conservative amino acid substitution, deletion or addition. More preferred is a silent substitution, deletion or addition, particularly preferred is a conservative substitution, and none of them alters the activity of the protein. Typical examples of the conservative substitution include substitution between two of aliphatic amino acids Ala, Val, Leu and Ile, exchange between hydroxyl residues Ser and Thr, exchange between acidic residues Asp and Glu, substitution between amide residues Asn and Gln, exchange between basic residues Lys and Arg, and substitution between aromatic residues Phe and Tyr.

The ubiquitin ligase of the present invention may comprise an additional peptide. Examples of the additional peptide include epitope peptides for labeling, such as a polyhistidine tag (His-tag), Myc and FLAG.

The ubiquitin ligase of the present invention can be prepared, for example, by a known genetic engineering technique, specifically by separately constructing a recombinant expression vector having an expressible insert of a gene encoding the protein of the above (a), and a recombinant expression vector having an expressible insert of a gene encoding the protein of the above (b), co-transferring these vectors into a suitable host cell for expression of recombinant proteins, and purifying a formed complex from the host cell or a culture medium of the host cell. A recombinant expression vector which can coexpress plural proteins can be also used.

Alternatively, the ubiquitin ligase of the present invention can be prepared, for example, by in vitro coupled transcription-translation system. In this case, a DNA fragment encoding the protein of the above (a) and a DNA fragment encoding the protein of the above (b) can be used with a known in vitro coupled transcription-translation system (for example, a system using cell-free extract of *Escherichia coli*, wheat germ cells or rabbit reticulocytes).

Whether the thus-obtained protein exists in a complex form and has ubiquitin ligase activity can be confirmed by a known method. The complex formation can be confirmed, for example, by analyzing the obtained protein in SDS-PAGE. When the results show plural protein bands, a complex is formed. The ubiquitin ligase activity can be confirmed, for example, by mixing the obtained protein with a ubiquitin activating enzyme (E1), a ubiquitin conjugating enzyme (E2), ATP and ubiquitin for reaction (for example, at 37° C. for about 5 minutes to about 1 hour). The presence or absence of the ubiquitin ligase activity depends on whether linear polyubiquitin chains are assembled or not after the reaction.

[Expression Vector]

The expression vector of the present invention at least contains a polynucleotide encoding (A) and/or (B).
(A) A protein which has a part of HOIP and at least has a UBA region and a RING-IBR-RING region thereof and which forms, with the following (B), a complex exhibiting ubiquitin ligase activity
(B) One or more kinds of proteins which individually form, with the above (A), a complex exhibiting ubiquitin ligase activity As the above (B), the protein of the above (b), which constitutes the ubiquitin ligase of the present invention, can be used. For example, preferred is a protein which has a region capable of binding to the UBA region of HOIP and which forms, with the above (A), a complex exhibiting ubiquitin ligase activity. More preferred is, for example, (I) HOIL-1L, or a protein which has a part of HOIL-1L and at least has a UBL region thereof and which forms, with the above (A), a complex exhibiting ubiquitin ligase activity, or (II) Sharpin, or a protein which has a part of Sharpin and at least has a UBL region thereof and which forms, with the above (A), a complex exhibiting ubiquitin ligase activity.

In the above (I), the protein which has a part of HOIL-1L and at least has a UBL region thereof and which forms, with the above (A), a complex exhibiting ubiquitin ligase activity, namely a partial HOIL-1L protein which has a UBL region of HOIL-1L and which forms, with the above (A), a complex exhibiting ubiquitin ligase activity is specifically a protein having a part of the amino acid sequence represented by SEQ ID NO: 1 and at least having a region of residues 70 to 130 of the amino acid sequence. For example, a protein having the amino acid sequence represented by SEQ ID NO: 5 is suitable. Also suitable is a protein which has an amino acid sequence the same as the amino acid sequence represented by SEQ ID NO: 5 except for having deletion, substitution or addition of one to several amino acids and which forms, with the above (A), a complex exhibiting ubiquitin ligase activity.

The polynucleotide encoding HOIL-1L is, for example, a polynucleotide having the base sequence represented by SEQ ID NO: 2. In this base sequence, the base sequence encoding the UBL region corresponds to a region of positions 208 to 390. Therefore, in the case where the above (I) is HOIL-1L, suitable as the HOIL-1L-encoding polynucleotide is, for example, a polynucleotide having the base sequence represented by SEQ ID NO: 2. In the case where the above (I) is a partial ROIL-1L protein having a UBL region of HOIL-1L, suitable as the polynucleotide encoding this partial protein is, for example, a polynucleotide having a part of the base sequence represented by SEQ ID NO: 2 and having a region of positions 208 to 390 of the base sequence.

The polynucleotide encoding a protein having the amino acid sequence represented by SEQ ID NO: 5 is, for example, a polynucleotide having the base sequence represented by SEQ ID NO: 6. Also suitable is a polynucleotide which hybridizes with a polynucleotide having a base sequence complementary to the base sequence represented by SEQ ID NO: 6 under stringent conditions and which encodes a partial HOIL-1L protein which forms, with the above (A), a complex exhibiting ubiquitin ligase activity.

In the above (II), the protein which has a part of Sharpin and at least has a UBL region thereof and which forms, with the above (A), a complex exhibiting ubiquitin ligase activity, namely a partial Sharpin protein which has a UBL region of Sharpin and which forms, with the above (A), a complex exhibiting ubiquitin ligase activity is specifically a protein having a part of the amino acid sequence represented by SEQ ID NO: 10 and at least having a region of residues 240 to 300 of the amino acid sequence. For example, a protein having the amino acid sequence represented by SEQ ID NO: 12 is suitable. Also suitable is a protein which has an amino acid sequence the same as the amino acid sequence represented by SEQ ID NO: 12 except for having deletion, substitution or addition of one to several amino acids and which forms, with the above (A), a complex exhibiting ubiquitin ligase activity.

The polynucleotide encoding Sharpin is, for example, a polynucleotide having the base sequence represented by SEQ ID NO: 11. In this base sequence, the base sequence encoding the UBL region corresponds to a region of positions 718 to 900. Therefore, in the case where the above (II) is Sharpin, suitable as the Sharpin-encoding polynucleotide is, for example, a polynucleotide having the base sequence represented by SEQ ID NO: 11. In the case where the above (II) is a partial Sharpin protein having a UBL region of Sharpin, suitable as the polynucleotide encoding this partial protein is, for example, a polynucleotide having a part of the base sequence represented by SEQ ID NO: 11 and having a region of positions 718 to 900 of the base sequence.

The polynucleotide encoding a protein having the amino acid sequence represented by SEQ ID NO: 12 is, for example, a polynucleotide having the base sequence represented by SEQ ID NO: 13. Also suitable is a polynucleotide which hybridizes with a polynucleotide having a base sequence complementary to the base sequence represented by SEQ ID NO: 13 under stringent conditions and which encodes a partial Sharpin protein which forms, with the above (A), a complex exhibiting ubiquitin ligase activity.

As the above (A), the protein of the above (a), which constitutes the ubiquitin ligase of the present invention, can be used. Preferred is, for example, a protein which has a part of the amino acid sequence represented by SEQ ID NO: 3 and at least has a region of residues 564 to 901 of the amino acid sequence and which forms, with the above (B), a complex exhibiting ubiquitin ligase activity. More preferred is, for example, a protein having the amino acid sequence represented by SEQ ID NO: 7. Also suitable is a protein which has an amino acid sequence the same as the amino acid sequence represented by SEQ ID NO: 7 except for having deletion, substitution or addition of one to several amino acids and which forms, with the above (B), a complex exhibiting ubiquitin ligase activity.

The polynucleotide encoding HOIP is, for example, a polynucleotide having the base sequence represented by SEQ ID NO: 4. In this base sequence, the base sequence encoding the region from the N-terminus of the UBA region to the C-terminus of the RING-IBR-RING region corresponds to a region of positions 1690 to 2703. Therefore, suitable as the polynucleotide encoding the above (A) is, for example, a polynucleotide having a part of the base sequence represented by SEQ ID NO: 4 and having a region of positions 1690 to 2703 of the base sequence.

The polynucleotide encoding a protein having the amino acid sequence represented by SEQ ID NO: 7 is, for example, a polynucleotide having the base sequence represented by SEQ ID NO: 8. Also suitable is a polynucleotide which hybridizes with a polynucleotide having a base sequence complementary to the base sequence represented by SEQ ID NO: 8 under stringent conditions and which encodes a partial HOIP protein which forms, with the above (B), a complex exhibiting ubiquitin ligase activity.

As used herein, the term "polynucleotide" is interchangeable with the term "gene", "nucleic acid" or "nucleic acid molecule". The polynucleotide of the present invention can be present in the form of RNA (for example, mRNA) or DNA (for example, cDNA or genomic DNA). DNA may be a double strand or a single strand. A single-stranded DNA or RNA may be a coding strand (sense strand) or a non-coding strand (antisense strand). The polynucleotide of the present invention may be ligated to a polynucleotide encoding a labeling tag (a tag sequence or a marker sequence) at the 5'- or 3'-terminus.

Hybridization can be performed according to a well-known method as described in Sambrook et al., Molecular Cloning, A Laboratory Manual, 3rd Ed., Cold Spring Harbor Laboratory (2001). Usually, as the temperature becomes higher and the salt concentration becomes lower, the conditions of hybridization become more stringent (this means that hybridization becomes harder to achieve), and accordingly, more homologous polynucleotides can be obtained. A suitable hybridization temperature varies with the base sequence and the length thereof, and for example, in the case where an 18-base DNA fragment encoding 6 amino acids is used as a probe, the temperature is preferably 50° C. or lower.

The procedure for "hybridizes under stringent conditions" means that a filter is incubated in a hybridization solution (50% formamide, 5×SSC (150 mM NaCl, 15 mM trisodium citrate), 50 mM sodium phosphate (pH 7.6), 5×Denhardt's solution, 10% dextran sulfate and 20 µg/ml denatured sheared salmon sperm DNA) at 42° C. overnight and then washed in 0.1×SSC at about 65° C.

Examples of a method for obtaining a polynucleotide used for the expression vector of the present invention include a method using amplification technique such as PCR. For example, based on the 5'- and 3'-terminal sequences of the base sequence of SEQ ID NO: 6 (or their complementary sequences), respective primers are designed, and using these primers and using genomic DNA, cDNA or the like as a template, PCR or the like is conducted to amplify a DNA region flanked by both primers. In this way, a DNA fragment containing a polynucleotide having the base sequence represented by SEQ ID NO: 6 can be obtained in a large amount.

The expression vector of the present invention includes the following expression vectors.
(i) The expression vector containing a polynucleotide encoding the protein of the above (A)
(ii) The expression vector containing a polynucleotide encoding the protein of the above (B)
(iii) The vector containing both of a polynucleotide encoding the protein of the above (A) and a polynucleotide encoding the protein of the above (B)

In the case where the protein of (B) is two or more kinds of proteins, polynucleotides separately encoding three or more kinds of proteins including (A) may be appropriately combined and inserted into a vector for preparation of a coexpression vector containing two or more kinds of polynucleotides.

The expression vector of the present invention is preferably a plasmid vector carrying a recognition sequence for RNA polymerase. In the case where the expression vector contains two or more kinds of polynucleotides, preferred is a plasmid vector carrying two or more recognition sequences for RNA polymerase. Such a plasmid vector can be appropriately selected from known vectors, and is easily available as a commercial plasmid vector.

The preparation method for recombinant expression vectors is not particularly limited, and examples thereof include methods using a plasmid, a phage or a cosmid. The kind of the vector is not particularly limited, and a vector that can be expressed in host cells can be appropriately selected. That is, depending on the kind of the host cell, a promoter sequence is appropriately selected to ensure the expression of a constituent protein of the ubiquitin ligase of the present invention, and the selected promoter sequence and a polynucleotide encoding the constituent protein of the ubiquitin ligase are inserted into any of various plasmids etc. for preparation of the expression vector of the present invention.

The expression vector preferably contains at least one selection marker. Examples of such a marker include a dihydrofolate reductase gene and a neomycin resistance gene for eukaryotic cell culture; and a tetracycline resistance gene and an ampicillin resistance gene for culture of *E. coli* and other bacteria. By use of such a selection marker, it can be confirmed whether the polynucleotide of the present invention has been transferred into host cells and then expressed therein without fail. Also, the polypeptide of the present invention may be expressed as a fusion polypeptide. For example, by use of green fluorescent protein (GFP) derived from *Aequorea coerulescens* as a marker, the polypeptide of the present invention may be expressed as a GFP fusion polypeptide.

The host cell described above is not particularly limited, and various known cells can be used preferably. Specific examples of the host cell include bacteria such as *Escherichia coli*, yeasts (budding yeast *Saccharomyces cerevisiae* and fission yeast *Schizosaccharomyces pombe*), nematodes (*Caenorhabditis elegans*), *Xenopus laevis* oocytes and animal cells (for example, CHO cells, COS cells and Bowes melanoma cells). The method for transferring the expression vector described above into host cells, i.e., the transformation method, is not particularly limited, and known methods such as electroporation, the calcium phosphate method, the liposome method and the DEAE dextran method can be used preferably.

In the case where the ubiquitin ligase of the present invention is a complex of two kinds of proteins, an expression vector containing two kinds of polynucleotides separately encoding (A) and (B) (coexpression vector) is transferred into a host cell, or both of an expression vector containing a polynucleotide encoding (A) and an expression vector containing a polynucleotide encoding (B) are co-transferred into a host cell.

In the case where the ubiquitin ligase of the present invention is a complex of three or more kinds of proteins, expression vectors each containing a polynucleotide encoding a different constituent protein of the complex are co-transferred into a host cell, or one or more expression vectors each containing a polynucleotide encoding a single protein are appropriately combined with one or more coexpression vectors so that all the polynucleotides encoding different constituent proteins of the complex are transferred into a host cell.

After a host cell into which all the polynucleotides encoding different constituent proteins of the complex have been transferred (transformant) is cultured, cultivated or bred, the ubiquitin ligase of the present invention can be collected and purified from the cultures etc. according to conventional methods (for example, filtration, centrifugation, cell disruption, gel filtration chromatography, ion exchange chromatography, etc.).

[Transformant]

The present invention provides a transformant with the expression vector of the present invention. The transformant of the present invention has at least one of the above-mentioned expression vectors of the present invention transferred therein, and does not need to simultaneously have all the polynucleotides encoding different constituent proteins of the ubiquitin ligase of the present invention. As used herein, the term "transformant" encompasses a cell, a tissue and an organ as well as an individual organism. The organism to be transformed is not particularly limited, and examples thereof include various microorganisms, plants and animals mentioned as examples of the host cell in the above.

Among the transformants of the present invention, the transformant with all the polynucleotides encoding different constituent proteins of the ubiquitin ligase of the present invention is suitable for use in production of the ubiquitin ligase of the present invention. It is preferable that the transformant stably expresses the ubiquitin ligase of the present invention, but the transformant may transiently express the same.

Here, as described above, the present inventor has been attempting to establish a LUBAC expression system that enables efficient expression of a recombinant LUBAC, namely a LUBAC expression system that enables efficient expression of a full-length HOIL-1L and a full-length HOIP, or a full-length Sharpin and a full-length HOIP and subsequent complex formation thereof, but has not yet succeeded. Specifically, as described in "Preparation of recombinant proteins" of MATERIALS AND METHODS of Non Patent Literature 1, the present inventor used to obtain LUBAC expressed in bacteria by three-step purification using nickel affinity gel, HiTrapQ and gel filtration. That is, for preparation of a recombinant LUBAC in the expression system described in Non Patent Literature 1, purification requires as many as three steps. From this description, it can be understood that the conventional expression system cannot provide efficient expression of a recombinant LUBAC. On the other hand, by use of the expression vector and the transformant of the present invention, the ubiquitin ligase of the present invention can be easily obtained by single-step purification with a nickel affinity gel, as shown in the Examples described below.

Therefore, the novel ubiquitin ligase, an expression vector therefor and a transformant therefor, each of which is provided by the present invention, are the first to enable efficient expression and high-yield purification of a ubiquitin ligase having linear polyubiquitination activity, and thus are a highly useful invention.

[Screening Method]

The screening method of the present invention at least comprises the steps of:
bringing a test substance into contact with the ubiquitin ligase of the present invention,
measuring the activity level of the ubiquitin ligase brought into contact with the test substance, and
comparing the above activity level to the activity level of the ubiquitin ligase not brought into contact with the test substance.

The screening method of the present invention enables simple and efficient screening for inhibitors of linear polyubiquitination.

The ubiquitin ligase of the present invention can be brought into contact with a test substance, for example, by dissolving or suspending the test substance in a solution containing the ubiquitin ligase. The contact time and the contact temperature are not particularly limited and can be appropriately selected. Preferably, a control group in which the ubiquitin ligase is not brought into contact with the test substance is prepared for the screening method of the present invention.

The activity level of the ubiquitin ligase can be measured by mixing the ubiquitin ligase to be analyzed, a ubiquitin activating enzyme (E1), a ubiquitin conjugating enzyme (E2), ATP and ubiquitin for reaction (for example, at 37° C. for about 5 minutes to about 1 hour), and quantifying assembled linear polyubiquitin chains. Commercially available E1, E2, ATP and ubiquitin may be also used.

By comparing the activity level of the ubiquitin ligase brought into contact with the test substance to that of the ubiquitin ligase not brought into contact with the test substance, it can be determined whether the test substance is an inhibitor of linear polyubiquitination. When the activity level of the ubiquitin ligase brought into contact with the test substance is lower than that of the ubiquitin ligase not brought into contact with the test substance, the test substance can be determined as an inhibitor of linear polyubiquitination. When the activity level is reduced to preferably 50% or less, and more preferably 25% or less, the test substance is determined as an inhibitor of linear polyubiquitination.

As described above, the present inventor clarified that, in the classical pathway of NF-κB activation, LUBAC ubiquitin ligase selectively binds to NEMO of the IKK complex, and then mediates linear polyubiquitination of NEMO, leading to IKK complex activation, followed by NF-κB activation (see Non Patent Literature 2), and also found out that the LUBAC-mediated linear polyubiquitination of NEMO selectively activates NF-κB. Since the ubiquitin ligase of the present invention is a complex of a partial HOIL-1L protein and a partial HOIP protein, a complex of a partial Sharpin protein and a partial HOIP protein, or a complex of a partial HOIL-1L protein, a partial Sharpin protein and a partial HOIP protein, each complex constituting LUBAC, the screening method of the present invention enables selection of substances that inhibit linear polyubiquitination of NEMO and thus selectively inhibit NF-κB activation. Therefore, the thus-selected inhibitors of linear polyubiquitination are extremely useful as an active ingredient candidate for preventive or therapeutic medicaments for various NF-κB-associated diseases.

Examples of the NF-κB-associated disease include rheumatoid arthritis, atopic dermatitis, inflammatory bowel disease (ulcerative colitis, Crohn's disease), bronchial asthma, malignant lymphoma and multiple myeloma.

EXAMPLES

Hereinafter, the present invention will be illustrated in detail by examples, but is not limited thereto. In the following Examples, a protein having the amino acid sequence from residues 1 to 191 of HOIL-1L (SEQ ID NO: 7) is called "HOIL-1L (1-191)" and a protein having the amino acid sequence from residues 474 to 1072 of HOIP (SEQ ID NO: 5) is called "HOIP (474-1072)". Also, the ubiquitin ligase of the present invention is called "petit-LUBAC".

Example 1

Construction of Petit-LUBAC Expression Vector

Figure 3:
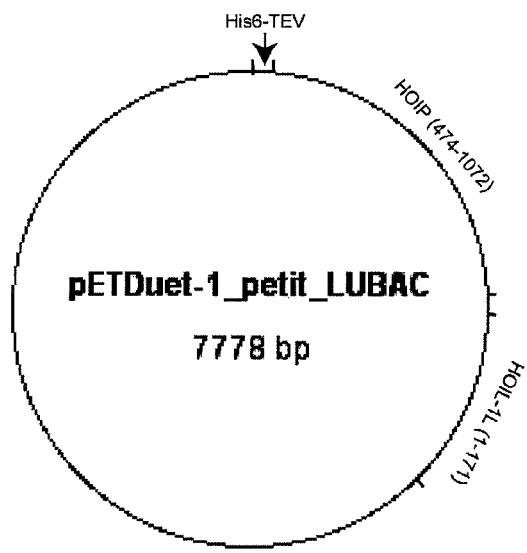
FIG. 3 shows the construct of pETDuet-1 petit-LUBAC.

A petit-LUBAC expression vector, pETDuet-1 petit-LUBAC was constructed by inserting a DNA encoding HOIP (474-1072) (SEQ ID NO: 6) downstream of His-Tag of MCS1 of pETDuet-1 vector (a vector designed for coexpression: manufactured by Novagen) and inserting a DNA encoding HOIL-1L (1-191) (SEQ ID NO: 8) into MCS2 thereof (see FIG. 3). The pETDuet-1 petit-LUBAC can express two kinds of proteins, that is, a protein having the sequence of "MRGSHHHHHHSQDPNSENLYFQ" (SEQ ID NO: 9) fused to the upstream (N-terminus) of HOIP (474-1072), and HOIL-1L (1-191).

Example 2

Expression and Purification of Petit-LUBAC

Expression and purification of petit-LUBAC were performed in the following procedures.
(1) BL21 (DE3) RIL was transformed with pETDuet-1 petit-LUBAC and seeded onto LB-ampicillin plates.
(2) One colony was cultured in 2 mL of an LB-ampicillin culture medium at 37° C. overnight.
(3) 1 mL of the culture medium of the above (2) was added to 50 mL of an LB-ampicillin culture medium and the mixture was cultured at 37° C. until the OD600 value reached 0.6.
(4) 50 mL of the whole culture medium of the above (3) was added to 1 L of an LB-ampicillin culture medium and the mixture was cultured at 28° C. until the OD600 value reached 0.6.
(5) IPTG was added at the final concentration of 0.4 mM and the culture was continued at 28° C. for additional 2 hours.
(6) The E. coli was collected and then suspended in 80 mL of a sonication medium (20 mM Tris-HCl pH 7.5, 150 mM NaCl, 5 mM 2-ME and protease inhibitor).
(7) The E. coli was lysed with a sonicator.
(8) The resulting E. coli lysate was centrifuged at 15,000 rpm at 4° C. for 20 minutes and the supernatant was collected (E. coli extract).
(9) To the E. coli extract, imidazole was added at the final concentration of 0.2 mM.
(10) After addition of 1 mL of Ni-NTA beads, the reaction was allowed to proceed at 4° C. for 1 hour.
(11) The beads were washed with wash solution 1 (20 mM Tris-HCl pH 7.5, 150 mM NaCl, 5 mM 2-ME and 3 mM imidazole).
(12) The beads were washed with wash solution 2 (20 mM Tris-HCl pH 7.5, 150 mM NaCl, 5 mM 2-ME and 20 mM imidazole).
(13) Elution was performed with an eluent (20 mM Tris-HCl pH 7.5, 150 mM NaCl, 5 mM 2-ME and 200 mM imidazole).
(14) The eluate was applied to a PD-10 column for buffer exchange with a buffer containing 20 mM Tris-HCl pH 7.5 and 1 mM DTT, and then preserved at −80° C.

Figure 4:
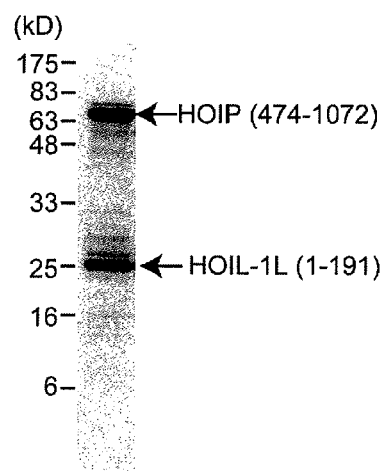
FIG. 4 shows the SDS-PAGE results of petit-LUBAC expressed in E. coli.

The purified product was subjected to SDS-PAGE. The results are shown in FIG. 4. As is clear from FIG. 4, two bands, that is, the band corresponding to HOIP (474-1072) and the band corresponding to HOIL-1L (1-191) were detected. These results showed that HOIP (474-1072) and HOIL-1L (1-191) form a complex and exist as petit-LUBAC.

Example 3

Confirmation of Linear Polyubiquitination Activity of Petit-LUBAC

The petit-LUBAC obtained in Example 2 was added at four concentration levels (including no addition) to a mixed solution of a ubiquitin activating enzyme (E1), UbCH5c (E2), ATP and ubiquitin, and then incubation was performed at 37° C. The reaction mixtures were subjected to electrophoresis for confirmation of polyubiquitin chain assembly.

Figure 5:
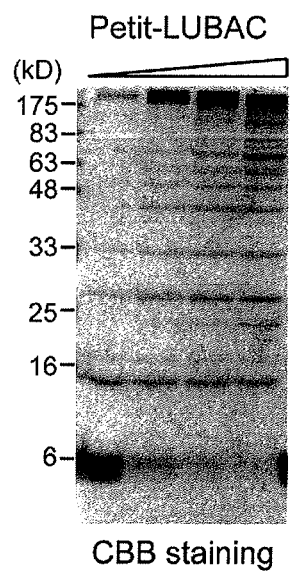
FIG. 5 shows results confirming the linear polyubiquitination activity of petit-LUBAC.

The results are shown in FIG. 5. In FIG. 5, the lanes correspond to no petit-LUBAC, and the low, middle and high levels of petit-LUBAC in this order from the left. As is clear from FIG. 5, in the case of addition of petit-LUBAC, the ladder-like bands appear in a manner dependent on the petit-LUBAC concentration, and this means that polyubiquitin chains were assembled. These results showed that petit-LUBAC has linear polyubiquitination activity.

Example 4

Construction of Petit-Sharpin Expression Vector

Figure 6:
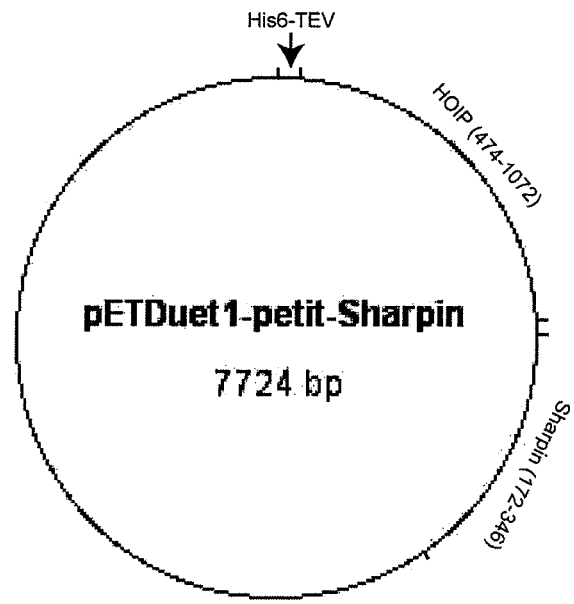
FIG. 6 shows the construct of pETDuet-1 petit-Sharpin.

A petit-Sharpin expression vector, pETDuet-1 petit-Sharpin was constructed by inserting a DNA encoding HOIP (474-1072) (SEQ ID NO: 6) downstream of His-Tag of MCS1 of pETDuet-1 vector (a vector designed for coexpression: manufactured by Novagen) and inserting a DNA encoding Sharpin (172-346) (SEQ ID NO: 13) into MCS2 thereof (see FIG. 6). The pETDuet-1 petit-Sharpin can express two kinds of proteins, that is, a protein having the sequence of "MRGSHHHHHHSQDPNSENLYFQ" (SEQ ID NO: 9) fused to the upstream (N-terminus) of HOIP (474-1072), and a protein having an additional methionine fused to the N-terminus of Sharpin (172-346).

Example 5

Expression and Purification of Petit-Sharpin

Expression and purification of petit-Sharpin were performed in the following procedures.
(1) BL21 (DE3) RIL was transformed with pETDuet-1 petit-Sharpin and seeded onto LB-ampicillin plates.
(2) One colony was cultured in 2 mL of an LE-ampicillin culture medium at 37° C. overnight.
(3) 1 mL of the culture medium of the above (2) was added to 50 mL of an LB-ampicillin culture medium and the mixture was cultured at 37° C. until the OD600 value reached 0.6.
(4) 50 mL of the whole culture medium of the above (3) was added to 1 L of an LB-ampicillin culture medium and the mixture was cultured at 28° C. until the OD600 value reached 0.6.

(5) IPTG was added at the final concentration of 0.4 mM and the culture was continued at 28° C. for additional 2 hours.

(6) The *E. coli* was collected and then suspended in 80 mL of a sonication medium (20 mM Tris-HCl pH 7.5, 150 mM NaCl, 5 mM 2-ME and protease inhibitor).

(7) The *E. coli* was lysed with a sonicator.

(8) The resulting *E. coli* lysate was centrifuged at 15,000 rpm at 4° C. for 20 minutes and the supernatant was collected (*E. coli* extract).

(9) To the *E. coli* extract, imidazole was added at the final concentration of 0.2 mM.

(10) After addition of 1 mL of Ni-NTA beads, the reaction was allowed to proceed at 4° C. for 1 hour.

(11) The beads were washed with wash solution 1 (20 mM Tris-HCl pH 7.5, 150 mM NaCl, 5 mM 2-ME and 3 mM imidazole).

(12) The beads were washed with wash solution 2 (20 mM Tris-HCl pH 7.5, 150 mM NaCl, 5 mM 2-ME and 20 mM imidazole).

(13) Elution was performed with an eluent (20 mM Tris-HCl pH 7.5, 150 mM NaCl, 5 mM 2-ME and 200 mM imidazole).

(14) The eluate was applied to a PD-10 column for buffer exchange with a buffer containing 20 mM Tris-HCl pH 7.5 and 1 mM DTT, and then preserved at −80° C.

Figure 7:
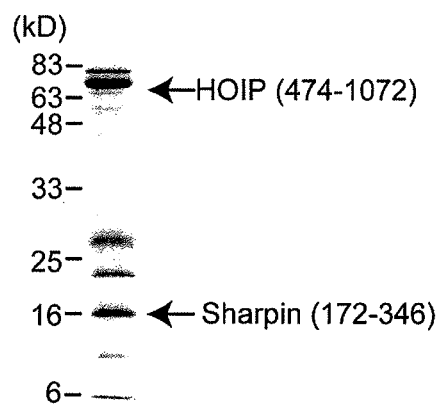
FIG. 7 shows the SDS-PAGE results of petit-Sharpin expressed in E. coli.

The purified product was subjected to SDS-PAGE. The results are shown in FIG. 7. As is clear from FIG. 7, two bands, that is, the band corresponding to HOIP (474-1072) and the band corresponding to Sharpin (172-346) were detected. These results showed that HOIP (474-1072) and Sharpin (172-346) form a complex and exist as petit-Sharpin.

Example 6

Confirmation of Linear Polyubiquitination Activity of Petit-Sharpin

The petit-Sharpin obtained in Example 5 was added at four concentration levels (including no addition) to a mixed solution of a ubiquitin activating enzyme (E1), UbCH5c (E2), ATP and ubiquitin, and then incubation was performed at 37° C. The reaction mixtures were subjected to electrophoresis for confirmation of polyubiquitin chain assembly.

Figure 8:
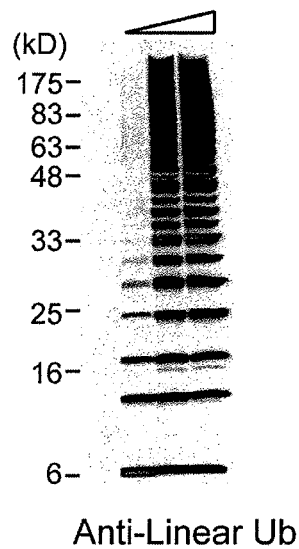
FIG. 8 shows results confirming the linear polyubiquitination activity of petit-Sharpin.

The results are shown in FIG. 8. In FIG. 8, the lanes correspond to no petit-Sharpin, and the low, middle and high levels of petit-Sharpin in this order from the left. As is clear from FIG. 8, in the case of addition of petit-Sharpin, the ladder-like bands appear in a manner dependent on the petit-Sharpin concentration, and this means that polyubiquitin chains were assembled. These results showed that petit-Sharpin has linear polyubiquitination activity.

The present invention is not limited to the aforementioned embodiments and examples, and various modifications can be made within the scope of the appended claims. Other embodiments obtainable by suitably combining technical means disclosed in different embodiments of the present invention are also included in the technical scope of the present invention. All the academic publications and patent literature cited in the above description are incorporated herein by reference.

INDUSTRIAL APPLICABILITY

The ubiquitin ligase of the present invention can be used for screening for active ingredient candidates for preventive or therapeutic medicaments for various NF-κB-associated diseases, and thus is extremely useful.

The invention claimed is:

1. An isolated ubiquitin ligase complex of the following (a) and (2), or a complex of the following (a), (1) and (2):
   (a) a protein consisting of the amino acid sequence of SEQ ID NO: 7;
   (1) a protein consisting of the amino acid sequence of SEQ ID NO: 1 or 5;
   (2) a protein consisting of the amino acid sequence of SEQ ID NO: 10 or 12.

2. A screening method for inhibitors of linear polyubiquitination, the method comprising the steps of:
   bringing a test substance into contact with the ubiquitin ligase of claim 1, a ubiquitin activating enzyme, a ubiquitin conjugating enzyme, ATP, and ubiquitin,
   measuring the activity level of the ubiquitin ligase, and
   comparing the activity level of the ubiquitin ligase in the presence of the test substance to the activity level of the ubiquitin ligase not brought into contact with the test substance,
   wherein when the activity level of the ubiquitin ligase brought into contact with the test substance is lower than that of the ubiquitin ligase not brought into contact with the test substance, the test substance can be determined as an inhibitor of linear polyubiquitination.

* * * * *